(12) United States Patent
Jacobs et al.

(10) Patent No.: US 9,256,966 B2
(45) Date of Patent: Feb. 9, 2016

(54) MULTIPARAMETRIC NON-LINEAR DIMENSION REDUCTION METHODS AND SYSTEMS RELATED THERETO

(75) Inventors: Michael A. Jacobs, Sparks, MD (US); Alireza Akhbardeh, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 124 days.

(21) Appl. No.: 14/000,011

(22) PCT Filed: Feb. 17, 2012

(86) PCT No.: PCT/US2012/025705
§ 371 (c)(1),
(2), (4) Date: Aug. 16, 2013

(87) PCT Pub. No.: WO2012/154260
PCT Pub. Date: Nov. 15, 2012

(65) Prior Publication Data
US 2013/0322728 A1 Dec. 5, 2013

Related U.S. Application Data

(60) Provisional application No. 61/443,748, filed on Feb. 17, 2011.

(51) Int. Cl.
| | | |
|---|---|---|
| *G06K 9/00* | (2006.01) | |
| *G06T 11/00* | (2006.01) | |
| *A61B 5/055* | (2006.01) | |
| *G06K 9/62* | (2006.01) | |
| *G06T 7/00* | (2006.01) | |
| *A61B 5/00* | (2006.01) | |
| *A61B 6/00* | (2006.01) | |

(52) U.S. Cl.
CPC ............ *G06T 11/003* (2013.01); *A61B 5/055* (2013.01); *G06K 9/6232* (2013.01); *G06T 7/0012* (2013.01); *A61B 5/7232* (2013.01); *A61B 6/502* (2013.01); *A61B 6/5217* (2013.01); *G06T 2207/10096* (2013.01); *G06T 2207/20064* (2013.01); *G06T 2207/30068* (2013.01)

(58) Field of Classification Search
USPC ................. 382/100, 128, 129, 130, 131, 132; 128/922; 378/4–27
See application file for complete search history.

(56) References Cited

U.S. PATENT DOCUMENTS

| | | | |
|---|---|---|---|
| 6,317,617 B1 | 11/2001 | Gilhuijs et al. | |
| 6,757,415 B1 * | 6/2004 | Rogers et al. | 382/130 |
| 6,763,128 B1 * | 7/2004 | Rogers et al. | 382/130 |

(Continued)

*Primary Examiner* — Anand Bhatnagar
(74) *Attorney, Agent, or Firm* — Mintz Levin Cohn Ferris Glovsky and Popeo, P.C.; Peter F. Corless; Richard B. Emmons

(57) ABSTRACT

Featured are methods and systems to multiparametric non-linear dimension reduction (NLDR) methods for segmentation and classification of radiological images. Such methods for segmentation and classification of radiological images, includes pre-processing of acquired image data; and reconstructing the acquired image data using a non-linear dimension reduction technique so as to yield an embedded image representing all of the acquired, where the acquired image data comprises a plurality of different sets of image data of the same region of interest. Such NLDR methods and systems are particularly suitable for the ability to combine multiple input images into a single unit for increased specificity of diagnosis.

12 Claims, 18 Drawing Sheets

(56) References Cited

U.S. PATENT DOCUMENTS

| | | |
|---|---|---|
| 7,949,181 B2 * | 5/2011 | Padfield et al. ............... 382/164 |
| 8,094,904 B2 * | 1/2012 | Slabaugh et al. ............. 382/130 |
| 8,379,993 B2 * | 2/2013 | Kendall et al. ................ 382/224 |
| 2002/0128550 A1 | 9/2002 | Van Den Brink et al. |
| 2009/0024022 A1 * | 1/2009 | Azar et al. .................... 600/420 |
| 2009/0087070 A1 * | 4/2009 | Slabaugh et al. ............. 382/132 |
| 2010/0061609 A1 * | 3/2010 | Shinagawa et al. ........... 382/131 |
| 2010/0329529 A1 | 12/2010 | Feldman et al. |
| 2013/0202173 A1 * | 8/2013 | Buckler et al. ................ 382/131 |

* cited by examiner

LLE Pipeline

FIG. 11A Source Image
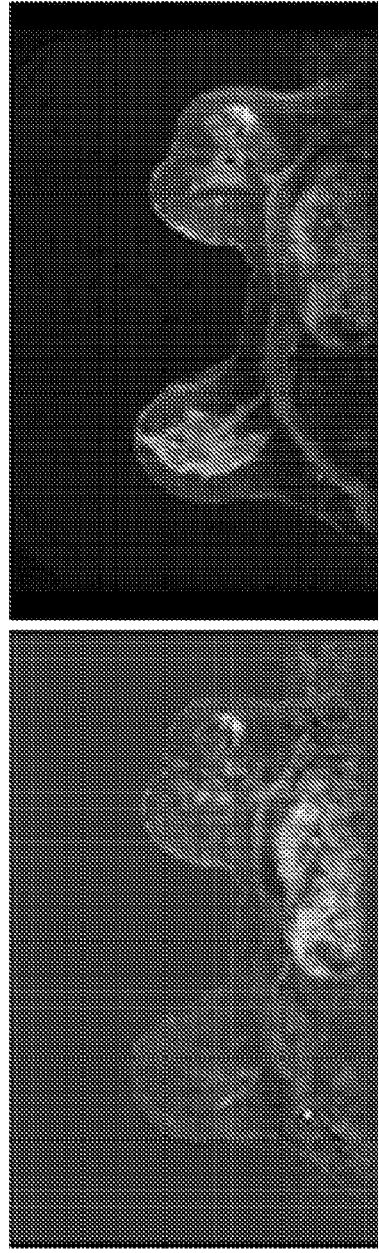
FIG. 11B Target Image
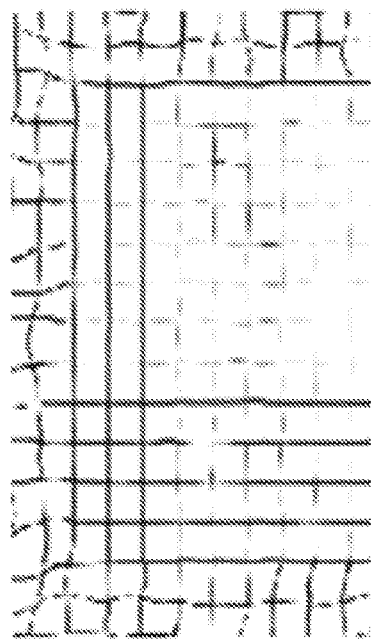
FIG. 11C Transformation map

MULTIPARAMETRIC NON-LINEAR DIMENSION REDUCTION METHODS AND SYSTEMS RELATED THERETO

CROSS-REFERENCE TO RELATED APPLICATIONS

This application is a 35 U.S.C. §371 U.S. national stage entry of International Application PCT/US2012/025705 (WO 2012/154260) having an International filing date of Feb. 17, 2012 which claims the benefit of U.S. Provisional Application Ser. No. 61/443,748 filed Feb. 17, 2011, the teachings of which are incorporated herein by reference.

FIELD OF INVENTION

The present invention generally relates to image reconstruction techniques, more particularly to multiparametric non-linear Dimension reduction methods for segmentation and classification of radiological images.

BACKGROUND OF THE INVENTION

Diagnostic radiological imaging techniques are powerful noninvasive tools with which to identify normal and suspicious regions within the body. The use of multiparametric imaging methods, which can incorporate different functional radiological parameters for quantitative diagnosis, has been steadily increasing [e.g., see M. Filippi and R. I. Grossman, "MRI techniques to monitor MS evolution: the present and the future," Neurology 58(8), 1147-1153 (2002); M. A. Jacobs, V. Stearns, A. C. Wolff, K. Macura, P. Argani, N. Khouri, T. Tsangaris, P. B. Barker, N. E. Davidson, Z. M. Bhujwalla, D. A. Bluemke, and R. Ouwerkerk, "Multiparametric magnetic resonance imaging, spectroscopy and multinuclear ((2)(3)Na) imaging monitoring of preoperative chemotherapy for locally advanced breast cancer," Acad. Radiol. 17(12), 1477-1485 (2010)].

Current methods of lesion detection include dynamic contrast-enhanced (DCE) magnetic resonance imaging (MRI) and/or positron emission tomography/computed tomography (PET/CT) images, which generate large amounts of data. Therefore, image-processing algorithms are required to analyze these images and play a key role in helping radiologists to differentiate normal from abnormal tissue. In multiparametric functional radiological imaging, each image sequence or type provides different information about a tissue of interest and its adjacent boundaries [e.g., see M. A. Jacobs, R. A. Knight, H. Soltanian-Zadeth, Z. G. Zheng, A. V. Goussev, D. J. Peck, J. P. Windham, and M. Chopp, "Unsupervised segmentation of multiparameter MRI in experimental cerebral ischemia with comparison to T2, Diffusion, and ADC MRI parameters and histopathological validation," J. Magn. Reson Imaging 11(4), 425-437 (2000); M. A. Jacobs, R. Ouwerkerk, A. C. Wolff, V. Stearns, P. A. Bottomley, P. B. Barker, P. Argani, N. Khouri, N. E. Davidson, Z. M. Bhujwalla, and D. A. Bluemke, "Multiparametric and multinuclear magnetic resonance imaging of human breast cancer: Current applications," Technol Cancer Res. Treat. 3(6), 543-550 (2004)]. For example, in multiparametric breast MRI, diffusion-weighted imaging (DWI) and DCE MRI provide information about cellularity and the vascular profile of normal tissue and tissue with lesions.

Similarly, PET/CT data provide information on the metabolic state of tissue. However, combining these data sets can be challenging, and because of the multidimensional structure of the data, methods are needed to extract a meaningful representation of the underlying radiopathological interpretation.

Currently, most computer-aided diagnosis (CAD) can act as a second reader in numerous applications, such as breast imaging [e.g., see R. H. El Khouli, M. A. Jacobs, and D. A. Bluemke, "Magnetic resonance imaging of the breast," Semin Roentgenol. 43(4), 265-281 (2008)]. Most CAD systems are based on pattern recognition and use Euclidean distances, correlation, or similar methods to compute similarity between structures in the data segmentation procedure. It has been shown, however, that methods based on Euclidean distance and other similarity measures cannot fully preserve the data structure, which negatively affects the performance of a CAD system.

Currently, there is limited technology with CAD systems that integrate multiparametric MRI and/or other radiological imaging procedures into highly specific dataset. For example, in breast cancer, typically, multiparametric MRI data consists of fat suppressed T2-weighted (T2WI), T1-weighted (T1WI), Dynamic Contrast Enhanced (DCE) and diffusion weighted imaging (DWI). These methods provide functional information that is currently not captured in existing CAD systems and CAD vendors do not use advanced machine learning methods for combining or visualizing the data. Moreover, the CAD systems use only small portions of the data for diagnosis. This limits the ability for a radiologist to be confident in gauging benign and malignant lesion boundaries and the extent of disease.

It thus would be desirable to provide new multiparametric non-linear Dimension reduction methods and systems for segmentation and classification of radiological images.

SUMMARY OF THE INVENTION

According to an aspect of the present invention, there are featured methods and systems for development of diagnostic tools for the early detection and classification of the different tissue types with high specificity and sensitivity and more particularly to method and systems for segmentation and classification of radiological images using tissue signature vectors from different tissues in multiple images and creating an embedded image for potential targets of disease. Early detection is the key to survival for cancer patients.

Such methods and systems are particularly suitable for the ability to combine multiple input images into a single unit for increased specificity of diagnosis; fast implementation of Advanced Machine Learning Methods for semi real time analysis; creation of embedded images for fully automatic segmentation of different tissue types; unsupervised tissue classification using geodesic angles determined from the topology of the data structure; determination of the contribution of each radiological parameter to the embedded image; addressing the partial volume effect using fuzzy boundaries between tissue types; and development of Advanced Machine Learning based CAD system.

According to another aspect/embodiment of the present invention, there is featured a method for segmentation and classification of radiological images. Such a method includes pre-processing of acquired image data; and reconstructing the acquired image data using a non-linear dimension reduction technique so as to yield an embedded image representing some or all of the acquired image data/image data sets, where the acquired image data comprises a plurality of different sets of image data of the same region of interest.

In further embodiments such preprocessing of image data includes compressing and equalizing image sizes using a wavelet transform. Also, such preprocessing of image data includes registering each of the plurality of different sets of image data including the same region of interest.

In yet further embodiments, such registering also includes resizing the number of slices in all planes to a desired size using orthogonal reslicing, registrating parameters estimation based on searching for best match between reference slices and target slices at a reslicing angle and plane (Xe), and non-uniform resampling including slice-by-slice angular reslicing and affine transformation of the target volume to another desired size using estimated registrating parameters. Such a reslicing angle is defined by ($\{\theta e(i)\}i=1:M1$) and in more particular embodiments the estimated reslicing angle(s)–$\theta e$ can be between 0 and 360 degree. Also, the reslicing plane (Xe) can be axial, coronal and/or sagittal. In yet further embodiments, angular reslicing at reslicing angles ($\{\theta e(i)\}i=1:M_r$), planes ($\{Xe(i)\}i=1:M_r$) and affine transformations ($\{T(i)\}i=1:M_r$) is applied to each of the target volume slices, where $M_r$ is the reference plane: the plane that reference image volume is scanned.

According to yet another aspect/embodiment of the present invention, there is featured a system for segmentation and classification of radiological images. Such a system includes one of a microprocessor, computer, digital processor or application specific integrated circuit (ASIC) and a software program for execution on the microprocessor, computer, digital processor or ASIC. Such a software program includes program code elements, criteria and instructions in a form that instructs the microprocessor, computer, digital processor or ASIC to perform functions of pre-processing of acquired image data; and reconstructing the acquired image data using a non-linear dimension reduction technique so as to yield an embedded image representing some or all of the acquired image data, where the acquired image data comprises a plurality of different sets of image data of the same region of interest. Reference in the specification or claims to one of a computer, digital processor, microprocessor or ASIC shall be understood to also include any of the other of computer, digital processor, microprocessor, ASIC or the like.

In further embodiments, such preprocessing of image data includes compressing and equalizing image sizes using a wavelet transform.

Also, such preprocessing of image data includes registering or co-registering each of the plurality of different sets of image data including the same region of interest. In further embodiments, such preprocessing of image data also includes registering or co-registering each of some or all of the different sets of image data including the same region of interest.

In yet further embodiments, such registering includes resizing the number of slices in some of, a plurality of or all planes to a desired size using orthogonal reslicing, registrating parameters estimation based on searching for best match between reference slices and target slices at a reslicing angle and plane, and non-uniform resampling including slice-by-slice angular reslicing and affine transformation of the target volume to another desired size using estimated registrating parameters. Such a reslicing angle is defined by ($\{\theta e(i)\}i=1:M1$) and in more particular embodiments the estimated reslicing angle(s) –$\theta e$ can be between 0 and 360 degree. Also, the reslicing plane (Xe) can be axial, coronal and/or sagittal.

In further embodiments, angular reslicing at reslicing angles ($\{\theta e(i)\}i=1:M_r$), planes ($\{Xe(i)\}i=1:M_r$) and affine transformations ($\{T(i)\}i=1:M_r$) is applied to each of the target volume slices, where $M_r$ is the reference plane: the plane that reference image volume is scanned.

According to yet other aspects of the present invention the above described methods and systems are implemented or carried out on a computer including an applications programs having instructions, criteria and code segments for performing the methods of the present invention. Also featured is a computer readable storage medium on which is stored such an applications program.

Other aspects and embodiments of the invention are discussed below.

DEFINITIONS

The instant invention is most clearly understood with reference to the following definitions:

As used in the specification and claims, the singular form "a", "an" and "the" include plural references unless the context clearly dictates otherwise.

As used herein, the term "comprising" or "including" is intended to mean that the compositions, methods, devices, apparatuses and systems include the recited elements, but do not exclude other elements. "Consisting essentially of", when used to define compositions, devices, apparatuses, systems, and methods, shall mean excluding other elements of any essential significance to the combination. Embodiments defined by each of these transition terms are within the scope of this invention.

ASIC as used in the specification and claims shall be understood to mean application specific integrated circuit.

CAD as used in the specification and claims shall be understood to mean computer-aided diagnosis.

CT or CAT as used in the specification and claims shall be understood to mean computed tomography or computer assisted tomography.

DCE-MRI as used in the specification and claims shall be understood to mean Dynamic Contrast Enhanced MRI.

DR as used in the specification and claims shall be understood to mean dimensionality reduction.

NLDR as used in the specification and claims shall be understood to mean Non-Linear Dimension Reduction.

PET as used in the specification and claims shall be understood to mean positron emission tomography ROI as used in the specification and claims shall be understood to mean region of interest.

Radiological images as used in the specification and claims shall be understood to mean images or image data acquired using MRI, X-Ray, CT, PET or UT imaging techniques.

A computer readable medium or a computer readable storage medium shall be understood to mean any article of manufacture that contains data that can be read by a computer or a carrier wave signal carrying data that can be read by a computer. Such computer readable media includes but is not limited to non-transitory media such as magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; paper media, such as punched cards and paper tape; or carrier wave signal received through a network, wireless network or modem, including radio-frequency signals and infrared signals.

USP shall be understood to mean U.S. Patent Number, namely a U.S. patent granted by the U.S. Patent and Trademark Office.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIGS. 11A-E includes various pictorial views of a demonstration of the co-registration of the MRI data using a locally affine model: (FIG. 11A) the T2WI source image; (FIG. 11B) the T1WI reference image; (FIG. 11C) warping map; (FIG. 11D) the final co-registered image and (FIG. 11E) the difference image obtained from subtracting the reference image from the registered image.

(FIG. 14A) effects of Sigma value on the dice similarity index between Diffusion Maps (DfM) based embedded image and the postcontrast (FIGS. 14B, C) effects of neighborhood size (K) on the dice similarity index between the embedded image and the postcontrast, respectively, for Isomap and LLE. Example input MRI data for the NLDR methods are shown in FIG. 1.

DESCRIPTION OF THE PREFERRED EMBODIMENT

Figure 1:
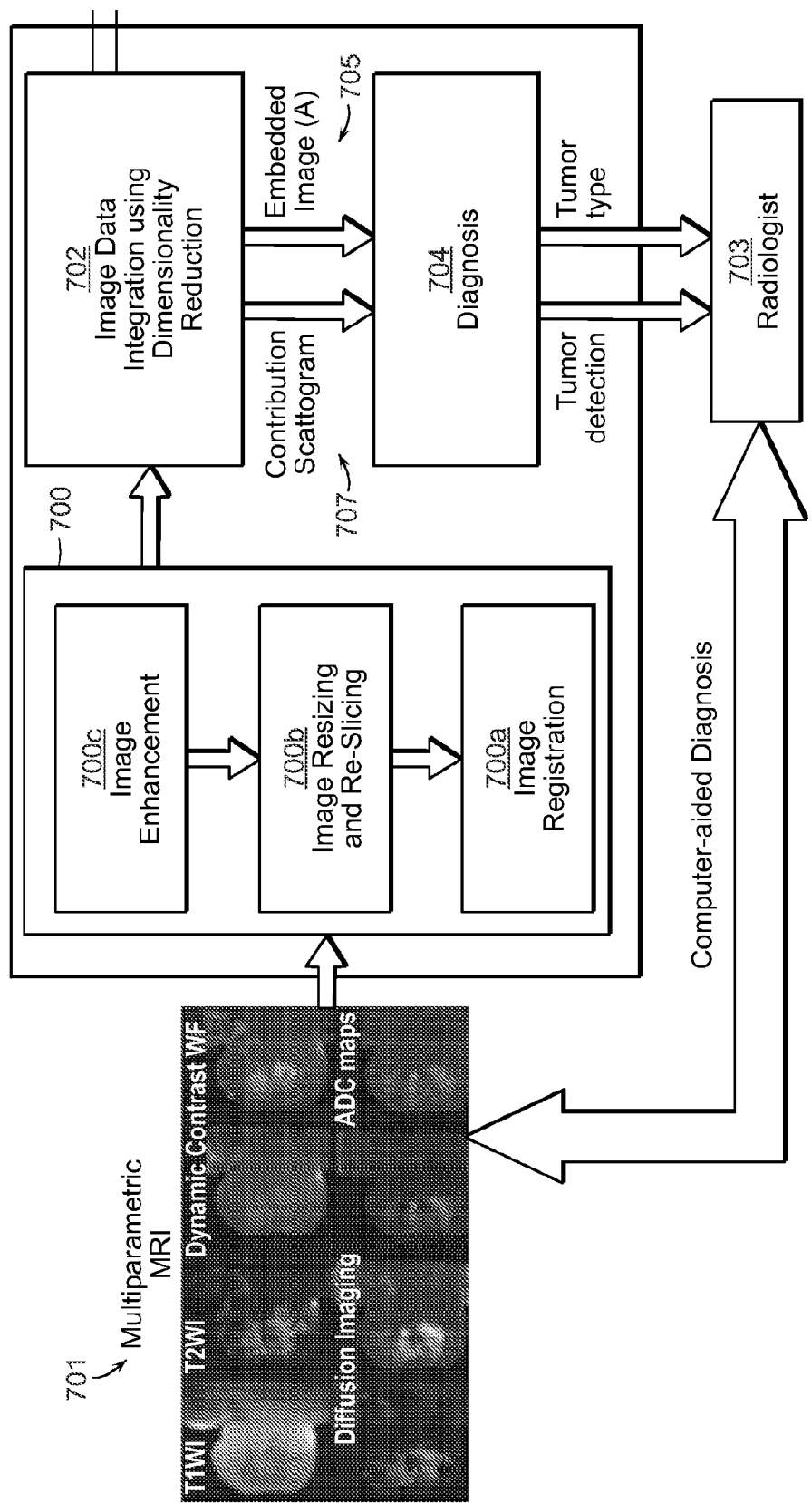
FIG. 1 is a high level flow diagram illustrating the NLDR method of the present invention.
Figure 2:
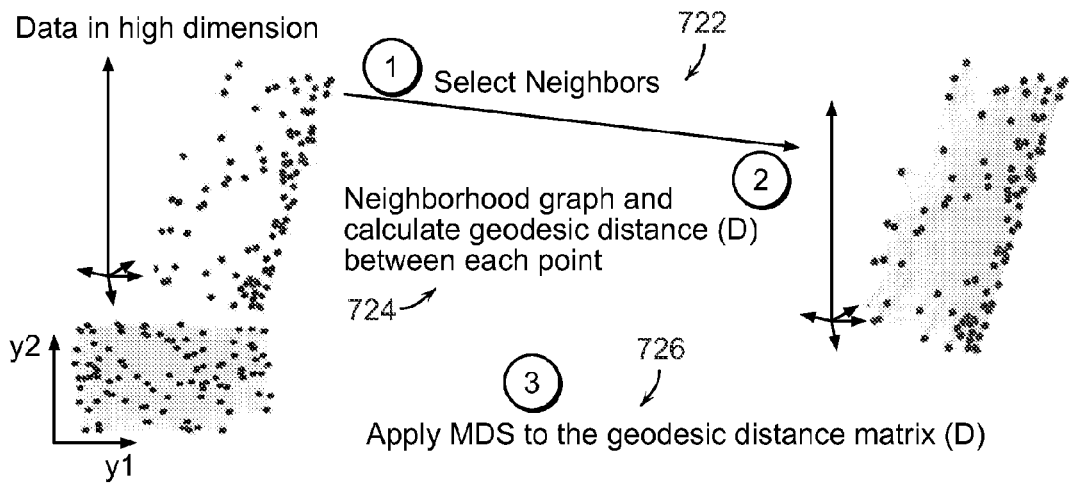
FIG. 2 is an illustrative view showing the steps of the Isomap algorithm used for mapping data into lower dimension m: (1) find K nearest neighbors for each data point $X_i$; (2) calculate pairwise geodesic distance matrix and reconstruct neighborhood graph using Dijkstra search algorithm; (3) apply Multidimensional scaling (MDS) on the reconstructed neighborhood graph (matrix D) to compute the low-dimensional embedding vectors.
Figure 3:
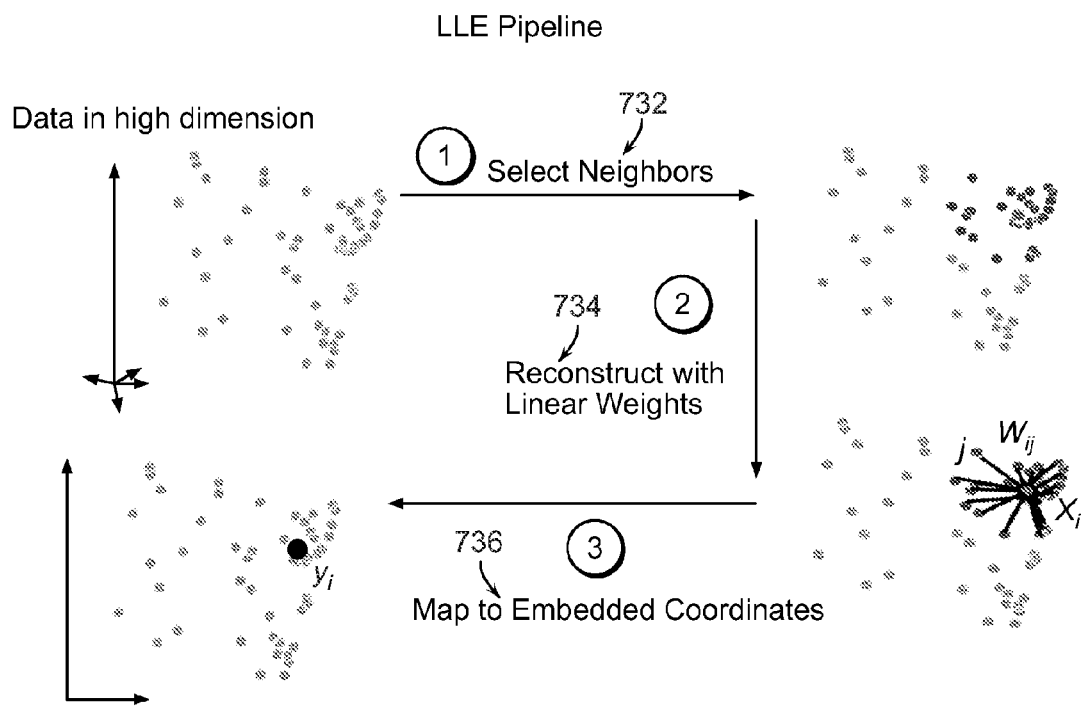
FIG. 3 is an illustrative view showing the steps of the LLE algorithm used for mapping data into lower dimension m: (1) search for K nearest neighbors for each data point $X_i$; (2) solve the constrained least-squares problem in Eq. (7) to obtain weights $W_{ij}$ that best linearly reconstruct data point $X_i$ from its K neighbors, (3) Compute the low-dimensional embedding vectors $Y_i$ best reconstructed by $W_{ij}$.

As described further herein, the present invention features methods and systems for development of diagnostic tools for the early detection and classification of the different tissue types with high specificity and sensitivity and more particularly to method and systems for segmentation and classification of radiological images using tissue signature vectors from different tissues in multiple images and creating an embedded image for potential targets of disease.

Such methods and systems are particularly suitable for the ability to combine multiple input images into a single unit for increased specificity of diagnosis; fast implementation of Advanced Machine Learning Methods for semi real time analysis; creation of embedded images for fully automatic segmentation of different tissue types; unsupervised tissue classification using geodesic angles determined from the topology of the data structure; determination of the contribution of each radiological parameter to the embedded image; addressing the partial volume effect using fuzzy boundaries between tissue types; and development of Advanced Machine Learning based CAD system.

In the following discussion, reference is made to block diagrams or high level flow diagrams that illustrate various methodologies for registering and/or reconstructing images according to the present invention. The flow charts/diagrams or block diagrams herein illustrate the structure of the logic of the different methodologies/inventions, which can be embodied in a computer program software or applications program for execution on a computer, digital processor, microprocessor or application specific integrated circuit (ASIC). Those skilled in the art will appreciate that the flow charts/diagrams and/or block diagrams illustrate the structures of the computer program code elements, including logic circuits on an integrated circuit, that function according to the present inventions. As such, the present inventions also are practiced in their essential embodiments by a machine component that renders the program code elements in a form that instructs a digital processing apparatus (e.g., computer) to perform a sequence of function step(s) corresponding to those shown in the flow diagrams and/or as described herein. Reference in the specification or claims to one of a computer, digital processor, microprocessor or ASIC shall be understood to also include any of the other of computer, digital processor, microprocessor, ASIC or the like.

As described herein, the methodology of the present invention is based in part on advanced machine learning techniques, and called "dimensionality reduction" (DR). Such a methodology preserves the prominent data structures and is useful for quantitatively integrating multimodal and multiparametric radiological images. Dimensionality reduction methods are a class of algorithms that use mathematically defined manifolds for statistical sampling of multidimensional classes to generate a discrimination rule of guaranteed statistical accuracy [P. Niyogi and N. K. Karmarkar, "An Approach to data reduction and clustering with theoretical guarantees," Proc. Int. Conf. Mach. Learn. 17, 679-686 (2000); H. S. Seung and D. D. Lee, "COGNITION: The manifold ways of perception," Science 290(5500), 2268-2269 (2000); J. Tenenbaum, V. Silva, and J. Langford, "A global geometric framework for nonlinear dimensionality reduction," Science 290(5500), 2319-2323 (2000); S. T. Roweis and L. K. Saul, "Nonlinear dimensionality reduction by locally linear embedding," Science 290(5500), 2323-2326 (2000); L. Tong and Z. Hongbin, "Riemannian manifold learning," IEEE Trans. Pattern Anal. Mach. Intell. 30(5), 796-809 (2008)].

DR can generate a two- or three-dimensional map, which represents the prominent structures of the data and provides an embedded image of meaningful low-dimensional structures hidden in the high-dimensional information [P. Niyogi and N. K. Karmarkar, "An Approach to data reduction and clustering with theoretical guarantees," Proc. Int. Conf. Mach. Learn. 17, 679-686 (2000)]. Pixel values in the embedded image are obtained based on distances over the manifold of pixel intensities in the higher dimension, and could provide higher accuracy in detecting soft and hard boundaries between tissues as compared to the pixel intensities of a single image modality. As described further herein the potential of DR methods of the present invention for medical image segmentation and the performance of such DR methods was investigated and compared using ISOMAP, local linear embedding (LLE), and DfM on high-dimensional synthetic data sets and on a group of patients with breast cancer (See Example 1).

Dimensionality reduction (DR) is the mathematical mapping of high-dimensional data into a meaningful representation of the intrinsic dimensionality (lower dimensional representation) using either linear or nonlinear methods (described below). The intrinsic dimensionality of a data set is the lowest number of images or variables that can represent the true structure of the data. For example, T1-weighted imaging (T1WI) and T2-weighted imaging (T2WI) are the lowest-dimension set of images that can represent anatomical tissue in the breast. Such dimensionality reduction methods are usable to detect the underlying structure of high-dimensional data, such as that resulting from MRI or PET images.

Referring now to FIG. 1, there is shown a high level flow diagram illustrating the NLDR methodology of the present invention. The acquired radiological image data 701 (e.g., multiparametric MRI image data) is input into the step of image processing, Step 700. In addition, such radiological image data also can be sent to the radiologist 703, technician, physician or the like (hereinafter the "or like' shall be understood). Thus, the radiologist 703, technician or physician can consider this image data as well as the embedded image 705 and/or contribution scattogram 707 in connection with the when diagnosing that patient or patient's condition (Step 704) including for that which can be found in the region of interest (e.g., tumor). The radiologist 703 or technician also can be controlling the performance of the image technique(s) used to acquire the image data. For example, the methods and systems of the present invention can lead to the detection of a tumor as well as providing information or detail whereby the type of tumor also can be determined during such diagnosing.

In addition to making an initial diagnosis, the methods and systems of the present invention also are usable to evaluate the ongoing or continuing condition of a patient (e.g., mammal) over time. In this way, such diagnosing can include assessing how the initially diagnosed condition is changing over time. For example, if the initial diagnosis involved the detection of a tumor, such methods and systems can be used to track any changes (e.g., volume or dimensions) to the tumor.

Such methods and systems of the present invention also provide a mechanism whereby the technician or radiologist can make an assessment(s) of the effectiveness of a treatment protocol that was initiated because of a diagnosis of the patient's condition. Thus such diagnosing also can include comparing the integrated image data that is previously acquired with the integrated image data that is more recently acquired or that acquired in a time wise fashion. For example, if the initial diagnosis included the detection of tumor, the assessment of the treatment protocol's effectiveness can be directed to determining if the treatment protocol is causing a reduction in size of the tumor. Such an assessment can be over an extended time period such as from the initiation of the treatment protocol to completion of treatment and/or termination of the treatment protocol.

As a result of such assessments, the radiologist, doctors or physicians also can determine if another treatment protocol should be used or combined with the existing treatment protocol. Thereafter, using the methods and systems of the present invention further assessments can be made as to the effectiveness of the changed treatment protocol. Thus, such diagnosing can include: (a) the acquired image data and/or embedded images/scattergram to determine the physical or medical condition of a patient, (b) determine the effectiveness of a treatment protocol, (c) monitoring the physical/medical condition of the patient as well as the effectiveness of a treatment protocol being implements and/or (d) and modifying, changing or replacing a treatment protocol based on such continuing or ongoing assessments.

In particular embodiments, such an image processing (step 700) includes image registration (Step 700a), image resizing and re-slicing (step 700b) and image enhancement (Step 700c). As provided herein, such image registration includes any of a number of techniques known to those skilled in the art, such as that discussed in connection with the following Example 1.

It also is within the scope of the present invention, to use the 3D registration methods and systems as described and taught in co-pending International patent application entitled "Methods and Systems for Registration of Radiological Images" (PCT/US2012/025705, filed Feb. 17, 2012), the teachings of which are incorporated by reference. Such methods embody reslicing-based non-rigid 3D registration of radiological images.

In such 3D registration methods and systems, global motion is modeled by an affine transform (rigid) while local motion and slices matching is estimated using non-uniform resampling of the pixel intensities of the target image volume along the reference plane. The reference plane is the plane that the reference image volume is scanned. The target plane can be any of axial, coronal, or sagittal and there is no need for the reference and target scanning planes to be the same.

In such 3D registration methods and systems, registration is performed by searching for a reslicing angles and reslicing planes that maximizes similarity between the reference image volume and the resliced target image volume. The estimated reslicing angles can be between 0 and 360 degree. By angular reslicing of the target image volume, the number of slices of the reference and target volumes will be the same and it deforms the target volume to morph it with the reference image volume. Such a reslicing-based non-rigid registration of the radiological images according to this aspect of the present invention is a useful tool to match slices location and thickness, and 3D registration of the image or object slices.

Such 3D registration methods and systems are particularly suitable for, for example: 3D reslicing of different modalities to match field of view (FOV); 3D reslicing of different modalities to match slice locations; 3D reslicing of different modalities to match slice thickness; 3D reslicing of different modalities to match image sizes; 3D reslicing different modalities using Wavelet transform and interpolation; 3D reslicing to correct displacement, rotation, and tilt of modalities; 3D slice by slice angular or radial reslicing to deform or warp and maximize similarity between the target and reference image; 3D reslicing of different modalities to transfer image data to the desired plane (e.g., Sagittal, Coronal, and/or axial) and 3D registration to preserve global and local volume. Such methods and systems of the present invention also are suitable for application to in-vivo to ex-vivo registration of different modalities.

In yet further embodiments such methods for 3D registration of multiparametric and modality images or objects includes acquiring image data in slices and processing the acquired image data. Such processing also includes resizing number of slices in all planes to a desired size using orthogonal reslicing, registrating parameters estimation based on searching for best match between reference slices and target slices at a reslicing angle and plane (Xe), and non-uniform resampling including slice-by-slice angular reslicing and affine transformation of the target volume to another desired size using estimated registrating parameters. Such a reslicing angle is defined by ($\{\theta e(i)\}i=1:M1$) and in more particular embodiments the estimated reslicing angle(s) $-\theta e$ can be between 0 and 360 degree. Also, the reslicing plane (Xe) can be axial, coronal and/or sagittal.

In further embodiments, angular reslicing at reslicing angles ($\theta e(i)i=1:M_r$), planes ($\{Xe(i)\}i=1:M_r$) and affine transformations ($\{T(i)\}i=1:M_r$) is applied to each of the target volume slices, where $M_r$ is the reference plane: the plane that reference image volume is scanned.

In further embodiments, the imaging technique is one of a MRI, CT, X-ray, PET and UT imaging technique In yet further embodiments, such acquiring image data includes acquiring image data of a given region of interest using one imaging technique and acquiring image data again for the given region of interest using a second imaging technique and wherein such processing includes processing the acquired image data from both imaging techniques so that the image data of said one technique is co-registered with the acquired data using the second imaging technique. In addition, said one imaging technique is one of a MRI, CT, X-ray, PET and UT imaging technique and the second imaging technique is the other of an MRI, CT, X-ray, PET and UT imaging technique.

In yet further embodiments, such acquiring image data includes acquiring image data for a given region of interest using one imaging technique and acquiring another image data for the given region of interest using the one imaging technique; wherein such processing includes processing the acquired image data for the one and the another imaging data. The imaging technique is one of a MRI, CT, X-ray, PET and UT imaging technique.

As to image resizing and re-slicing (step 700b) and image enchantment (Step 700c), these processes embody any of a number of techniques known to those skilled in the art and otherwise appropriate for the intended use as discussed further herein as well as those hereinafter developed and otherwise appropriate for the intended use.

It should be understood that a multiplicity of images or image slices are processed so that after such image processing, some or all of the image data is integrated or combined using the dimensionality reduction methodology of the present invention so as to yield an embedded image 705 and/or a contribution scattergram 707 (Step 702). In particular embodiments, a plurality or a multiplicity of sets of image data are acquired and at least a plurality of such sets of image data or the multiplicity of sets of data, are integrated or combined using the dimensionality reduction methodology of the present invention so as to yield an embedded image 705 and/or a contribution scattergram 707.

As indicated herein, the image data being integrated can be acquired using the same or different image modalities or techniques. For example, image data is acquired using MRI and CT imaging techniques and thereafter integrated so that a single embedded image 705 is output to the technician or radiologist for evaluation and embodying image data acquired using both imaging techniques. This is not limiting as the sets of image data being acquired can involve the use of one imaging technique, two or more different imaging techniques (e.g., 2, 3 or 4 different imaging techniques), the use of one general imaging technique (MRI) but involving different imaging techniques within the general technique (e.g., DCE-MRI), or a combination of such techniques).

It also is within the scope of the present invention to use the 3D registration methodology described herein, so that the image data from these different imaging modalities can be co-registered for integration.

Also, as is known to those skilled in the art, certain imaging modalities or techniques require/involve repetitive acquisition of a plurality or a multiplicity of image data for a given slice. Thereafter, the repetitively acquired plurality or a multiplicity of image data for a given slice is then processed and combined in the appropriate fashion so as to provide a single slice of image data.

The methods and systems of the present invention also are adaptable for use with any of a number of imaging modalities and/or techniques as are known to those skilled in the art. The following describes such methods of the present invention and the integration of image data in more detail.

Mathematically, a data set, $X \subset R^{D(x_1, x_2, \ldots x_n) = D(Images)}$ where $x_1, x_2, \ldots, x_n$=T1W1, T2WI, DWI, DCE MRI or others, and such a data set has an intrinsic dimensionality, d<D, if X can be defined by d points or parameters that lie on a manifold. $R^D$ refers to D dimensional space with real numbers. Typically, a manifold learning method is used to determine points or locations within a dataset X (e.g., MRI, PET, etc.) lying on or near the manifold with intrinsic (lower) dimensionality, d, that is embedded in the higher dimensional space (D). By definition, a manifold is a topological space that is locally Euclidean, i.e., around every point, there exists a neighborhood that is topologically the same as the open unit ball in Euclidian space. Indeed, any object that can be "charted" is a manifold [J. M. Lee, *Riemannian Manifolds: An Introduction to Curvature* (Springer, New York, 1997)].

Dimensionality reduction methods map dataset $X=\{x_1, x_2, \ldots x_n\} \subset R^{D(images)}$ into a new dataset, $Y=\{y_1, y_2, \ldots, y_n\} \subset R^d$, with dimensionality d, while retaining the geometry of the data as much as possible. Generally, the geometry of the manifold and the intrinsic dimensionality d of the dataset X are not known. In recent years, a large number of methods for DR have been proposed, which belong to two groups: linear and nonlinear which are briefly discussed herein.

Linear DR

Linear DR methods assume that the data lie on or near a linear subspace of some high-dimensional topological space. Some examples of linear DR methods are: Principal components analysis (PCA) [I. T. Jolliffe, *Principal Component Analysis* (Springer, N.Y., 2002)], linear discriminant analysis (LDA); [R. Fisher, "The use of multiple measurements in taxonomic problems," Ann. Eugen. 7, 179-188 (1936)], and multidimensional scaling (MDS) [R. Breiger, S. Boorman, and P. Arabie, "An algorithm for clustering relational data with applications to social network analysis and comparison with multidimensional scaling," J. Math. Psychol. 12(3), 328-383 (1975)].

Principal Component Analysis (PCA)

PCA finds a lower dimensional subspace that best preserves the data variance, and where the variance in the data is maximal. In mathematical terms, PCA attempts to find a linear mapping, M, which maximizes the sum of the diagonal elements (trace) of the following matrix:

$$M^T * \Sigma * M \quad (1)$$

under the constraint that $|M|=1$, where E is the covariance matrix of the D dimensional data and $X=[x_1, x_2, \ldots, x_N]$ is the zeroed mean. "*" represents the multiplication of two matrices. Reports have shown that the linear map M could be estimated using d eigenvectors, i.e., PCA, of the covariance matrix of the data:

$$\Sigma * V = \lambda V \quad (2)$$

$\lambda$ is the eigenvalue corresponding to the eigenvector V. The data X now can be mapped to an embedding space by $$Y = M * X, \quad (3)$$

where the first d largest PCAs are stored in the columns of matrix M. If the size of the $\Sigma$ is high, the computation of the eigenvectors would be very time consuming. An approximation method proposed by, Partridge et al., termed "Simple PCA," which uses an iterative Hebbian approach to estimate the principal eigenvectors of E is used to address this concern [M. Partridge and R. A. Calvo, "Fast dimensionality reduction and simple PCA," Intel'. Data Anal. 2(1-4), 203-214 (1998)].

PCA has been applied in several applications for pattern recognition and the intrinsic dimension of the data is distributed on a linear manifold; however, if the data are not linear, then an overestimation of the dimensionality could occur or PCA could fail [A. Sehad, A. Hadid, H. Hocini, M. Djeddi, and S. Ameur, "Face recognition using neural networks and eigenfaces," Comput. Their Appl. n, 253-257 (2000); A. Santhanam and M. Masudur Rahman, 2006 IEEE/RSJ International Conference on the Intelligent Robots and Systems (2006) (unpublished)].

Multidimensional Scaling (MDS)

Classical MDS determines the subspace ($Y \subset R^{d_1}$) that best preserves the interpoint distances by minimizing the cost function of error between the pair-wise Euclidean distances in the low-dimensional and high-dimensional representation of the data. That is, given $X \subset R^{D(images)}$, MDS attempts to preserve the distances into lower dimensional space, $Y \subset R^d$, so that inner products are optimally preserved.

The cost function is defined as $$E(X, Y) = \sum_{ij} \left( \|x_i - x_j\| - \|y_i - y_j\| \right)^2 \quad (4)$$

where $\|x_i-x_j\|$ and $\|y_i-y_j\|$ are Euclidean distances between data points in the higher and lower dimensional space, respectively. Similar to PCA, the minimization can be performed using the eigen decomposition of a pairwise distance matrix as shown below $$B = \tau(D) = X^T * X,$$

$$B * V = \lambda V,$$

$$M = [V_1, V_2, \ldots V_d],$$

$$Y = M * X \quad (5)$$

where B is the pair-wise distance matrix, V is the eigenvectors, M is the eigenvalues, and Y, the first d largest eigenvectors stored in the columns of matrix M, and the embedded data in the reduced dimension, respectively.

MDS has been applied in several applications in pattern recognition and data visualization [P. Niyogi and N. K. Karmarkar, "An Approach to data reduction and clustering with theoretical guarantees," Proc. Int. Conf. Mach. Learn. 17, 679-686 (2000); H. S. Seung and D. D. Lee, "COGNITION: The manifold ways of perception," Science 290(5500), 2268-2269 (2000); J. Tenenbaum, V. Silva, and J. Langford, "A global geometric framework for nonlinear dimensionality reduction," Science 290(5500), 2319-2323 (2000); S. T. Roweis and L. K. Saul, "Nonlinear dimensionality reduction by locally linear embedding," Science 290(5500), 2323-2326 (2000); J. Bruske and G. Sommer, "Intrinsic dimensionality estimation with optimally topology preserving maps," IEEE Trans. Pattern Anal. Mach. Intell. 20(5), 572-575 (1998); M. Belkin and P. Niyogi, "Laplacian eigenmaps and spectral techniques for embedding and clustering," Adv. Neural Inf. Process. Syst. 14, 585-591 (2002)]. The most frequently used linear DR methods (PCA and MDS) were selected to compare with nonlinear DR techniques in the present invention.

Nonlinear Dimension Reduction

Nonlinear techniques for DR do not rely on the linearity assumption for segmentation. As a result, more complex embedding of high-dimensional data can be identified where linear methods often fail. There are a number of nonlinear techniques, such as Isomap [J. Tenenbaum, V. Silva, and J.

Langford, "A global geometric framework for nonlinear dimensionality reduction," Science 290(5500), 2319-2323 (2000); M. H. C. Law and A. K. Jain, "Incremental nonlinear dimensionality reduction by manifold learning," IEEE Trans. Pattern Anal. Mach. Intell. 28(3), 377-391 (2006)], locally linear embedding [S. T. Roweis and L. K. Saul, "Nonlinear dimensionality reduction by locally linear embedding," Science 290(5500), 2323-2326 (2000); L. K. Saul and S. T. Roweis, "Think globally, fit locally: Unsupervised learning of low dimensional manifolds," J. Mach. Learn. Res. 4, 119-155 (2003)], Kernel PCA [B. Schölkopf, A. Smola, and K.-R. Müller, "Nonlinear component analysis as a Kernel eigenvalue problem," Neural Comput. 10(5), 1299-1319 (2006)], diffusion maps [R. R. Coifman, S. Lafon, A. B. Lee, M. Maggioni, B. Nadler, F. Warner, and S. W. Zucker, "Geometric diffusions as a tool for harmonic analysis and structure definition of data: Diffusion maps," Proc. Natl. Acad. Sci. U.S.A. 102(21), 7426-7431 (2005); B. Nadler, S. Lafon, R. R. Coifman, and I. G. Kevrekidis, "Diffusion maps, spectral clustering and reaction coordinates of dynamical systems," Appl. Comput. Harmon. Anal. 21(1), 113-127 (2006)], Laplacian Eigenmaps [M. Belkin and P. Niyogi, "Laplacian eigenmaps and spectral techniques for embedding and clustering," Adv. Neural Inf. Process. Syst. 14, 585-591 (2002)], and other techniques [Z. Zhang and H. Zha, "Principal manifolds and nonlinear dimensionality reduction via tangent space alignment," SIAM J. Sci. Comput. (USA) 26(1), 313-338 (2004); T. Kohonen, "Self-organized formation of topologically correct feature maps," Biol. Cybern. 43(1), 59-69 (1982)].

The following briefly describes these different non-linear techniques.

Isometric Feature Mapping (Isomap)

As indicated herein, the DR technique maps dataset X into a new dataset, Y, with dimensionality d, while retaining the geometry of the data as much as possible. If the high dimensional data lies on or near a curved smooth manifold, Euclidean distance does not take into account the distribution of the neighboring data points and might consider two data points as close, whereas their distance over the manifold is much larger than the typical interpoint distance. Isomap overcomes this by preserving pairwise geodesic (or curvilinear) distances between data points using a neighborhood graph [J. Tenenbaum, V. Silva, and J. Langford, "A global geometric framework for nonlinear dimensionality reduction," Science 290 (5500), 2319-2323 (2000)]. By definition, Geodesic distance (GD) is the distance between two points measured over the manifold and generally estimated using Dijkstra's shortest-path algorithm [E. W. Dijkstra, "A note on two problems in connexion with graphs," Numer. Math. 1(1), 269-271 (1959)].

The Geodesic distances (GDs) between the data points are computed by constructing a neighborhood graph, G (every data point $x_i$ is connected to its k nearest neighbors, $x_{ij}$), where, the GDs between all data points form a pair-wise GD matrix. The low-dimensional space Y is then computed by applying multidimensional scaling (MDS) while retaining the GD pairwise distances between the data points as much as possible. To accomplish this, the error between the pair-wise distances in the low-dimensional and high-dimensional representation of the data are minimized using the following equation:

$$\Sigma(\|x_i - x_{ij}\| - \|y_i - y_{ij}\|)$$

Figure 12A:
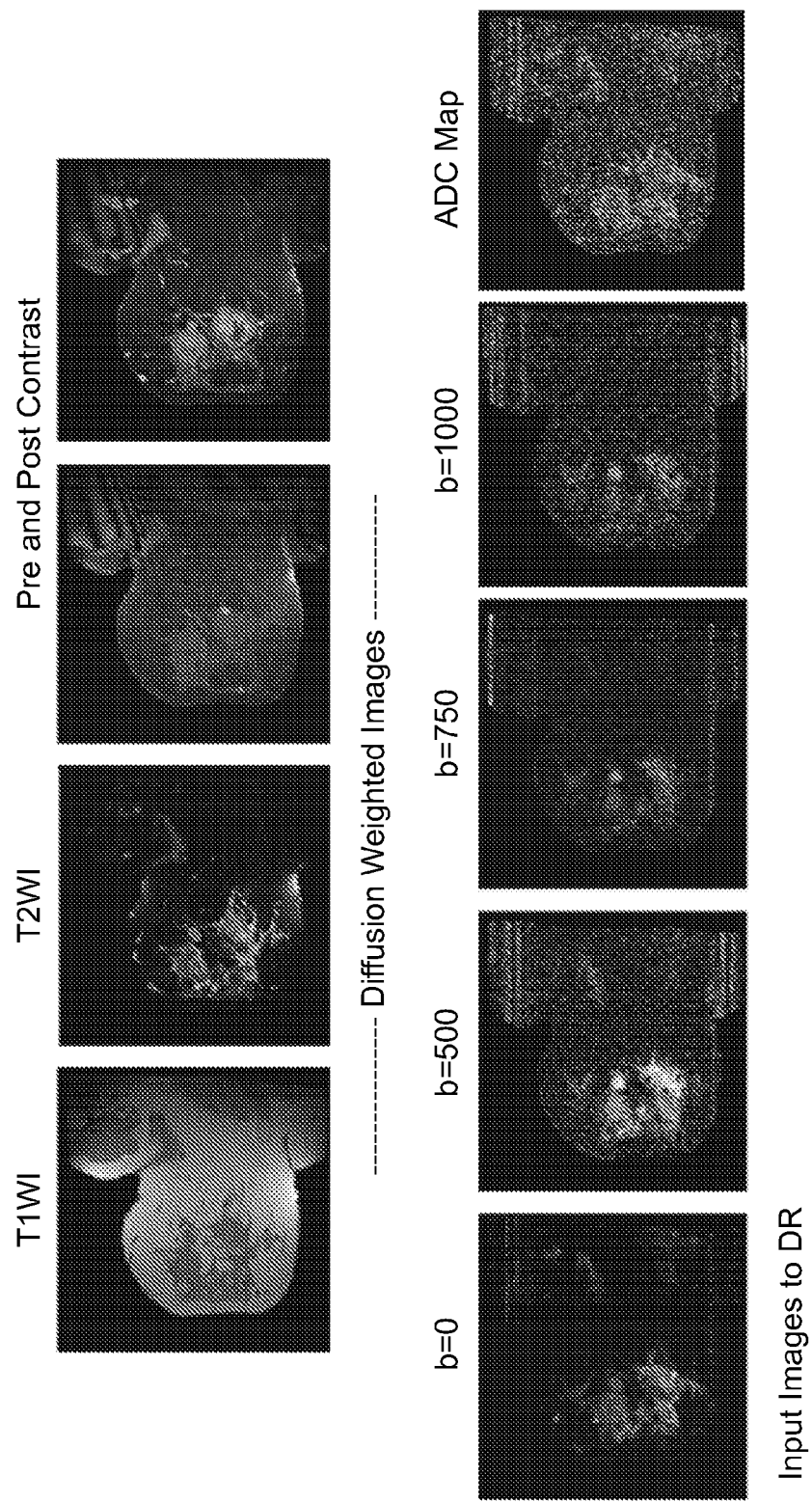
FIGS. 12A-B are various pictorial views showing typical multiparametric MRI data (FIG. 12A) and (FIG. 12B) resulting embedded images and scattergrams for a malignant breast case from three NLDR algorithms Dfm, Isomap, and LLE). The lower scattergram shown is derived from Isomap. Clear demarcation of the lesion and surrounding breast are shown.
Figure 12B:
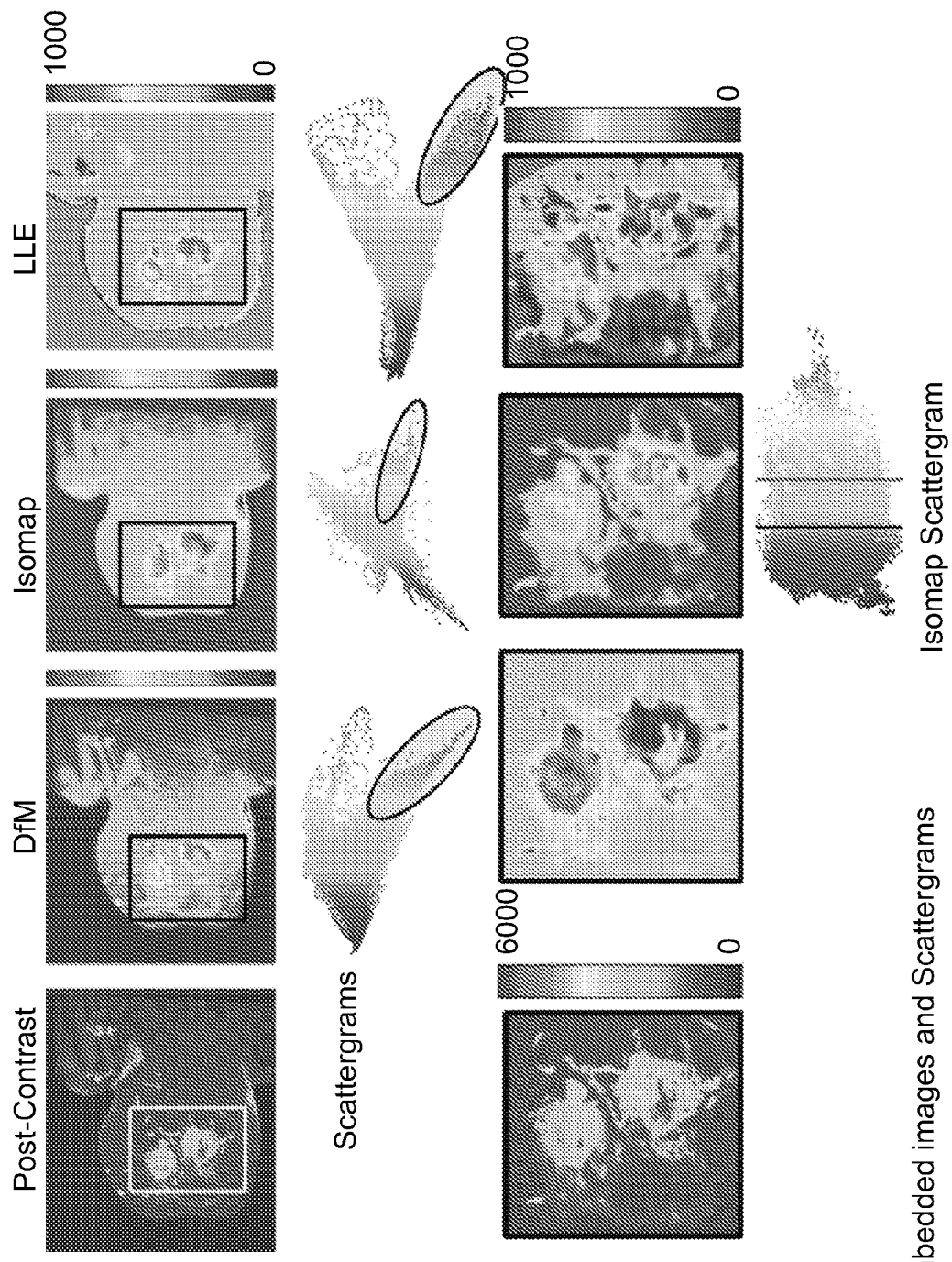

This minimization is performed using various methods, such as the eigen-decomposition of the pair-wise distance matrix, the conjugate gradient method, or a pseudo-Newton method [T. F. Cox, *Multidimensional Scaling*, 1st ed. (Chapman and Hall, London, 1994)]. The eigen decomposition is used for the implementation and FIG. 12 illustrates the steps used to create the Isomap embedding, namely select neighbors (Step 722), neighborhood graph and calculate geodesic distance (D) between each point (Step 724) and apply MDS to the geodesic distance matrix (Step 726).

Locally Linear Embedding (LLE)

LLE preserves the local properties of the data, which allows for successful embedding of non-convex manifolds. LLE assumes that the global manifold can be reconstructed by "local" or small connecting regions (manifolds) that are overlapped. That is, if the neighborhoods are small, the manifolds are approximately linear. LEE performs linearization to reconstruct the local properties of the data by using a weighted summation of the k nearest neighbors for each data point. This approach of linear mapping of the hyperplane to a space of lower dimensionality preserves the reconstruction weights. Thus, this allows the reconstruction weights, $W_i$, to reconstruct data point $y_i$ from its neighbors in the reduced dimension.

Therefore, to find the reduced (d) dimensional data representation Y, the following cost function is minimized for each point $x_i$:

$$\varepsilon(W) \sum_{i=1}^{n} \|x_i - \sum_{j=1}^{k} w_{ij} x_{ij}\| \quad (7)$$

subject to two constraints, $$\sum_{i=1}^{k} w_{ij} = 1 \text{ and } w_{ij} = 0$$

when $x_j \notin R^{D(images)}$. Where X is input data, n is the number of points, and k is the neighborhood size. The optimal weights matrix W (n×k), subject to these constraints, is found by solving a least-squares problem [S. T. Roweis and L. K. Saul, "Nonlinear dimensionality reduction by locally linear embedding," Science 290(5500), 2323-2326 (2000)].

Figure 13A:
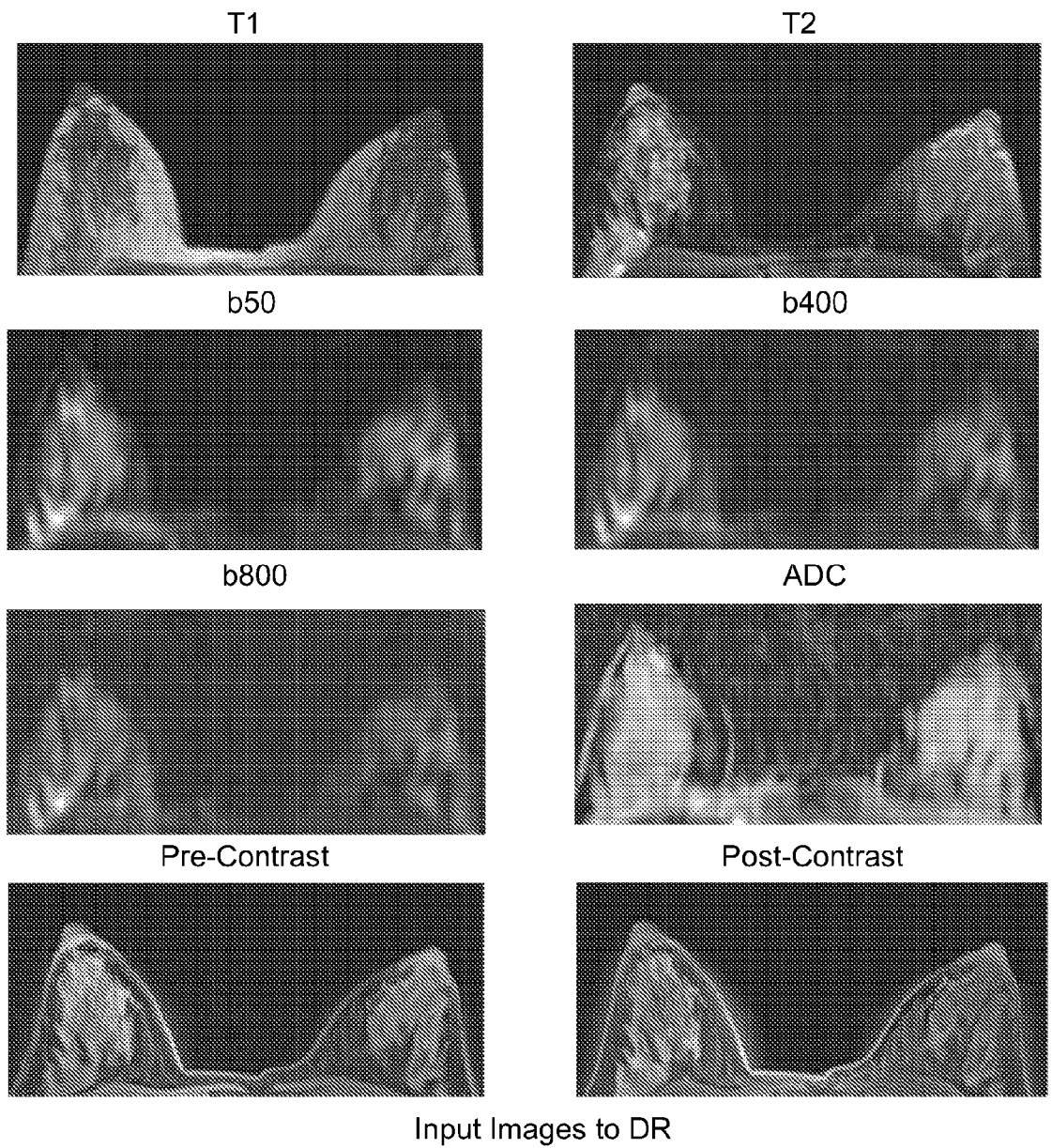
FIG. 13A, B are various views showing (FIG. 13A) typical axial multiparametric MRI data from a patient with no breast lesion and (FIG. 13B) resulting embedded images and scattergrams demonstrating the separation of fatty and glandular tissue in the embedded image, the scattergram shown is derived from ISOMAP.
Figure 13B:
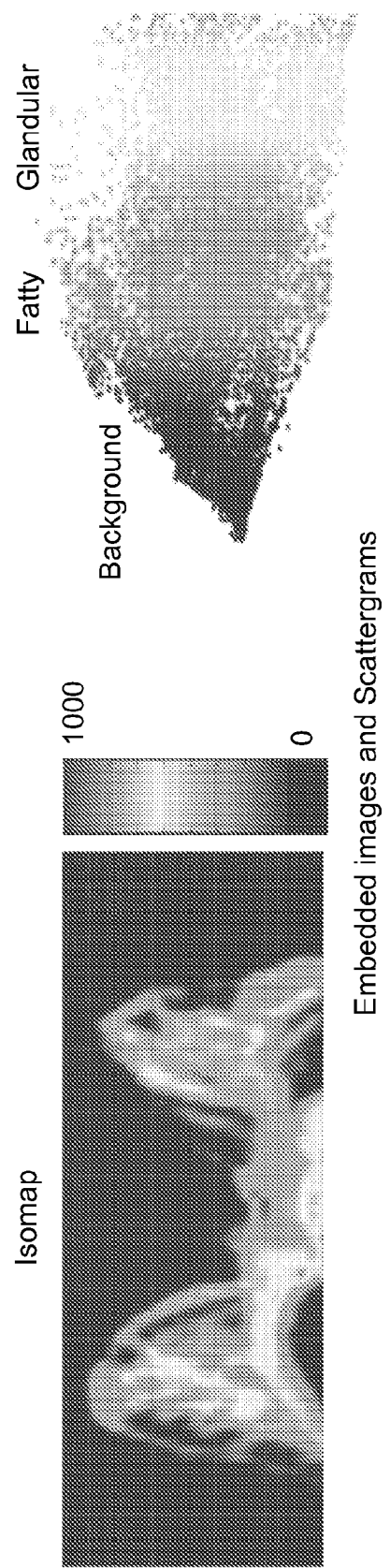

Then, the embedding data (Y) is calculated by calculating the eigenvectors corresponding to the smallest d nonzero eigenvalues of the following matrix:

$$E = (I-W)^{T*}(I-W),$$

$$E^*V = \lambda V$$

$$M = [V_1, V_2, \ldots V_d],$$

$$Y = M^*X, \quad (8)$$

where I is the identity matrix and W is the weights matrix (n×k). There is shown in FIG. 13 the steps for LLE, namely select neighbors (Step 732), reconstruct with linear weights (Step 734) and map to embedded coordinates (Step 736).

Diffusion Maps (DfM)

Diffusion maps find the subspace that best preserves the so-called diffusion interpoint distances based on defining a Markov random walk on a graph of the data called a Laplacian graph [R. R. Coifman, S. Lafon, A. B. Lee, M. Maggioni, B. Nadler, F. Warner, and S. W. Zucker, "Geometric diffusions as a tool for harmonic analysis and structure definition of data: Diffusion maps," Proc. Natl. Acad. Sci. U.S.A. 102(21), 7426-7431 (2005); B. Nadler, S. Lafon, R. R. Coifman, and I.

G. Kevrekidis, "Diffusion maps, spectral clustering and reaction coordinates of dynamical systems," Appl. Comput. Harmon. Anal. 21(1), 113-127 (2006)]. These maps use a Gaussian kernel function to estimate the weights (K) of the edges in the graph;

$$K_{ij} = e^{-\frac{\|x_i - x_j\|^2}{2e^2}} \quad 1 \le i, j \le L, \qquad (9)$$

where L equals the number of multidimensional points and σ is the free parameter, sigma. In the next step, the matrix K is normalized such that its rows add up to 1

$$p_{ij}^{(1)} = \frac{K_{ij}}{\sum_{n=1}^{L} K_{in}}, \qquad (10)$$

where P represents the forward transition probability of t-time steps of a random walk from one data point to another data point. Finally, the diffusion distance is defined as:

$$D_{ij}^{(2)} = \sum_{r=1}^{L} \frac{(p_{ir}^{(t)} - p_{jr}^{(t)})^2}{\Psi(x_r)}, \qquad (11)$$

$$\psi(x_m) = \frac{\sum_{j=1}^{L} P_{jm}}{\sum_{k=1}^{L} \sum_{j=1}^{L} P_{jk}},$$

Here, the high density portions of the graph defined by the diffusion distance have more weight, and pairs of data points with a high forward transition probability have a smaller diffusion distance. The diffusion distance is more robust to noise than the geodesic distance because it uses several paths throughout the graph to obtain the embedded image. Based on spectral theory about the random walk, the embedded image of the intrinsic dimensional representation Y can be obtained using the d nontrivial eigenvectors of the distance matrix D $$Y: x \rightarrow \{\lambda_2 V_2, \ldots \lambda_d V_d\}. \qquad (12)$$

The DfM graph is a fully connected, eigenvector $v_1$ of the largest eigenvalue ($\lambda_1$=1) that is discarded, and the remaining eigenvectors are normalized by their corresponding eigenvalues.

DR-Based Manifold Unfolding

As indicated herein, the DR methods map high dimensional data to a lower dimension while preserving data structure. This property of DR can be used to unfold N-dimensional manifolds into a lower dimension. To illustrate DR capabilities, the advantages and disadvantages of each linear and nonlinear DR method for manifold unfolding, three well-known synthetic datasets—the Swiss-roll, 3D-clusters, and sparse data sets—were used to test each of the methods and determine which one(s) should be used on the clinical data in the below described Example 1.

DR-Based Multidimensional Image Data Integration

Figure 14A:
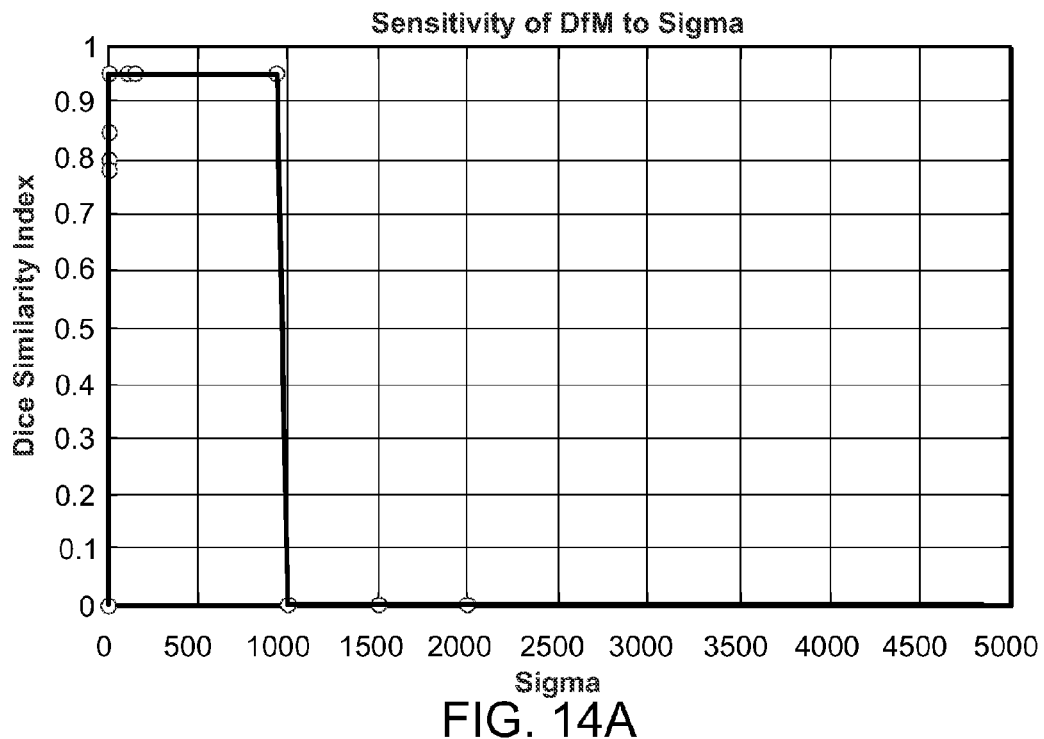
FIGS. 14A-C are graphical views showing a demonstration of the sensitivity of NLDR methods to control parameters.
Figure 14B:
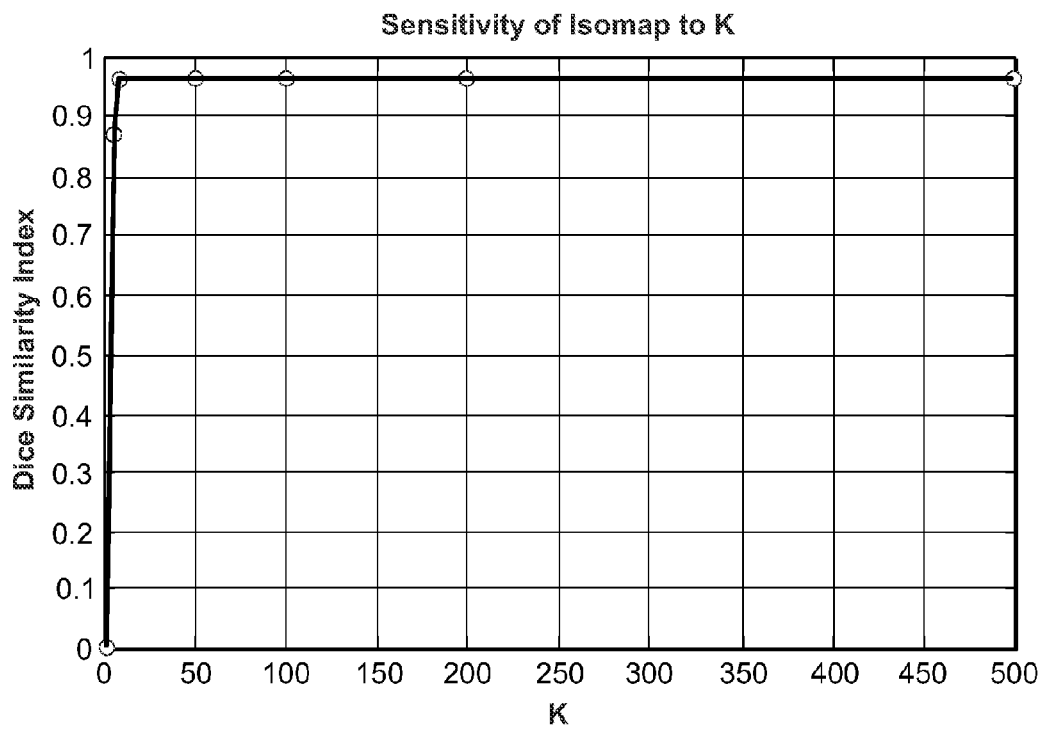

By using DR and its manifold unfolding ability, the integrate multidimensional image data can be integrated for visualization. The DR scheme of the present invention is shown in FIG. 14A and includes two stages: (1) preprocessing—Step 802 (enhancement, co-registration, and image resizing); and (2) dimensionality reduction—Step 804 to obtain an embedded image for soft tissue segmentation. The logic or steps following Step 804 and shown in FIG. 14B are descriptive of the process being carried out during the described Example 1 to assess the effectiveness of the information determined from, or obtained using, the DR scheme. For example, the tumor region of interest (ROI) on the embedded image or compared with the corresponding binary image for performing a performance evaluation.

FIG. 14B shows the steps for automated extraction of tumor boundaries [A and B in FIG. 14B] from the embedded and postcontrast images. The same procedure is used for fatty and glandular breast tissue. As indicated herein, to test for overlap and similarity, the Dice similarity metric was used as described further herein [L. R. Dice, "Measures of the amount of ecologic association between species," Ecology 26(3), 297-302 (1945)]. The DS measure is defined as $$DS = 2\frac{A \cap B}{A + B} = 2\frac{TP}{2TP + FP + FN}, \qquad (13)$$

where A is the tissue boundary in the embedded image, B is the tissue boundary in the postcontrast image, TP is the true positive, FP is the false positive, and FN is the false negative.

Preprocessing Steps (Step 802)

Image Enhancement (Step 802a)

Since artifacts and noise can degrade radiological images and may make identification and diagnosis difficult, smoothing filters, such as 2D median and mean filters, can be used to denoise and smooth noisy images. In particular, MRI images can have large $B_1$ inhomogeneities that can obscure anatomical structures. To estimate true signal and correct $B_1$-inhomogeneity effects, a modified version was used of the "local entropy minimization with a bicubic spline model (LEMS)," developed by Salvado et al. [O. Salvado, C. Hillenbrand, Z. Shaoxiang, and D. L. Wilson, "Method to correct intensity inhomogeneity in MR images for atherosclerosis characterization," IEEE Trans. Med. Imaging 25(5), 539-552 (2006)].

LEMS is based on modeling the bias field, β, as a bicubic spline and the RF coil geometry as a sufficiently close rectangular grid of knots scattered across the image (X). Initialization of LEMS begins with a fourth-order polynomial function estimation of the tissue voxel, where the background is excluded. Optimization of the bicubic spline model is performed in piecewise manner. LEMS first identifies a region within the image with the highest signal to noise ratio (SNR) and assigns it to Knot $K_1$ to ensure that a good local estimate of the field β is obtained. LEMS then adjusts the signal at $K_1$, based on an 8×8 neighborhood of knots, to locally minimize the entropy of X in $K_1$ and its neighbors. LEMS repeats the same routine for other knots with high SNR and minimizes the entropy within the corresponding knot ($K_1$) neighbor, as well as in prior knots ($\{K_1\}_{1 \le j < 1}$) until either the maximum number of iterations are reached or the knot entropies do not change significantly.

Equalizing Image Sizes Using Wavelet Transform (Step 802b)

As image sizes can vary, there is a need for a method to equalize image sizes with less loss of spatial and textural information. If any image is smaller than the desired size (N), data interpolation should be used to upsize the image to N. There are several well-known interpolation methods, such as nearest-neighbor, bilinear, and bicubic. However, if any of the images are larger than the desired size (N), the image should be downsized, which causes loss of spatial and textural information. To avoid this problem, a powerful multi-resolution analysis using wavelet transforms can be used [S. G. Mallat, "A theory for multi-resolution signal decomposition—The wavelet representation," IEEE Trans. Pattern Anal. Mach. Intell. 11(7), 674-693 (1989); S. G. Mallat, *A Wavelet Tour of Signal Processing*, The Sparse Way, 3rd ed. (Academic, n, 2008)].

Wavelets are mathematical functions that decompose data into different frequency components, thereby facilitating the study of each component with a resolution matched to its scale [S. G. Mallat, "A theory for multi-resolution signal decomposition—The wavelet representation," IEEE Trans. Pattern Anal. Mach. Intell. 11(7), 674-693 (1989)]. The continuous wavelet transform of a square integrable function, $f(t)$, is defined as:

$$wf(s, t) = \int_{-\infty}^{\infty} f(t) \frac{1}{\sqrt{\delta}} \psi\left(\frac{t-\tau}{s}\right) \quad (14)$$

where s and t are the scale (or frequency) and time variable, respectively. The function $\psi(t)$, is called a wavelet and must satisfy the admissibility condition, that is, it must be a zero-meaned and square-integrable function.

In practical applications, the parameters s and t must be discretized. The simplest method is dyadic. By using this method, the fast wavelet transform (FWT) is defined as $$wf[n, 2^j] = \sum_{m=0}^{N-1} f[m]\psi_j[m-n] = f[n] * \psi_j \quad (15)$$

where $$\psi_j[n] = \psi\left(\frac{n}{2^j}\right)$$

and $f[n]$ is a sequence with a length of N (discrete time function), and the * sign represents a circular convolution.

To implement a fast-computing transform, the FWT algorithm was used. At each level of decomposition, the FWT algorithm filters data with two filters, called h[n] and g[n]. The filter h[n], a conjugate mirror filter, is a low-pass filter, and thus, only low-frequency (coarse) components can pass through it; conversely, g[n] is a high-pass filter to pass high frequency (detail) components. The dyadic wavelet representation of signal $a_0$ is defined as the set of wavelet coefficients up to a scale J ($=\log_2 N$), plus the remaining low-frequency information [$1 \leq j \leq J$].

For image processing, the 1D FWT was first applied to the rows of the image. Then, the same transform was applied to the columns and diagonals of each component. Therefore, three high-pass (detail) components were obtained corresponding to vertical, horizontal, and diagonal, and one approximation (coarse) component. FIGS. 15A-D outlines with block diagrams the procedure using the 1D and 2D FWT. By using the inverse FWT (IFWT), we could reconstruct the original image in a different scale and resolution (see FIGS. 15A-D) and when reformatted, there was no loss of resolution.

Co-Registration Methods (Step 802*c*)

For co-registration of the different modalities/parameters, a modified non-rigid registration technique developed by Periaswamy and Farid was used [S. Periaswamy and H. Farid, "Elastic registration in the presence of intensity variations," IEEE Trans. Med. Imaging 22(7), 865-874 (2003)]. The present invention is not limited to this particular co-registration technique as it is within the scope of the present invention to use any of a number of co-registration techniques as known to those in the art and as otherwise appropriate for the intended use. It also is within the scope of the present invention to use the 3D registration methods described herein as well as any co-registration methods hereinafter developed.

The method is based on both geometric (motion) and intensity (contrast and brightness) transformations. The geometric model assumes a locally affine and globally smooth transformation. The local affine model is based on motion estimation. Model parameters are estimated using an iterative scheme that uses nonlinear least squares optimization to compute model parameters [K. Horn, *Robot Vision* (MIT, Cambridge, Mass., 1986)]. In order to deal with the large amount of motion and capture both large and small-scale transformations, a Gaussian pyramid was built for both source and target images. Model parameters were initially estimated at the coarsest level and were used to warp the source image at the next level of the pyramid and update the model parameters at each level of the pyramid. This multi-scale approach enabled registration of different images, such as T1WI, T2WI, and DWI. A set of derivative filters designed for multidimensional differentiation was used to decrease noise and to improve the resultant registration.

Embedded Image and Scattergram Reconstruction (Step 804)

After the preprocessing (e.g., image enhancement, wavelet-based compression, and image registration), the radiological images are used as inputs for the DR methods. The embedded image is constructed by projecting the features (image intensities) from N-dimensional space to a one dimensional embedding space, using the results from the DR methods (see FIG. 14A). The resultant embedding points then reconstructed the embedded image by reforming the embedded data matrix from the size $$L \times 1 \text{ to } \frac{L}{2} \times \frac{L}{2}$$

If data is mapped from N-dimensional space into two-dimensional space, one will obtain an unfolded version of the data manifold with different clusters [J. Tenenbaum, V. Silva, and J. Langford, "A global geometric framework for nonlinear dimensionality reduction," Science 290(5500), 2319-2323 (2000); S. T. Roweis and L. K. Saul, "Nonlinear dimensionality reduction by locally linear embedding," Science 290 (5500), 2323-2326 (2000)].

Example 1

The multiparametric breast MRI segmentation described herein in connection with Example 1, used the methods and systems described herein including that described above. More particularly, the DR scheme shown in FIG. 4A including the two stages: (1) preprocessing—Step 802 (enhancement, co-registration, and image resizing); and (2) dimensionality reduction—Step 804 to obtain an embedded image for soft tissue segmentation, was used. As also indicated hereinabove, the logic or steps following Step 804 and shown in FIG. 4B are descriptive of the process carried out during the processes described for Example 1 to assess the effectiveness of the information determined from, or obtained using, the DR scheme. For example, the tumor region of interest (ROI) on the embedded image is compared with the corresponding binary image for performing a performance evaluation.

Multiparametric Breast MRI Segmentation

Clinical Subjects

In this multiparametric breast MRI segmentation research study, twenty-five patients were scanned as part of the study. Also, all of the subjects signed written, informed consent, and the study was approved by the local IRB. Of the twenty-five patients, twenty-three had breast tumors of which 19 were malignant and 4 were benign, and two patients had no masses.

Multiparametric MRI Imaging Protocol

The MRI scans were performed on a 3T magnet, using a dedicated phased array breast coil with the patient lying prone with the breast in a holder to reduce motion. The MRI sequences were: fat suppressed (FS) T2WI spin echo (TR/TE=5700/102) and fast spoiled gradient echo (FSPGR) T1WI (TR/TE=200/4.4, 2562, slice thickness, 4 mm, 1 mm gap); diffusion-weighted (TR/TE=5000/90 ms, b=0.500-1000, 1282, ST=6 mm); and finally, precontrast and postcontrast images FSPGR T1WI (TR/TE=20/4, matrix=5122, slice thickness, 3 mm) were obtained after intravenous administration of a GdDTPA contrast agent [0.2 ml/kg (0.1 mmol/kg)].

The contrast agent was injected over 10 second, with MRI imaging beginning immediately after completion of the injection and the acquisition of at least 14 phases. The contrast bolus was followed by a 20 cc saline flush.

The DCE protocol included 2 min. of high temporal resolution (15 s per acquisition) imaging to capture the wash-in phase of contrast enhancement. A high spatial resolution scan for 2 min. then followed, with additional high temporal resolution images (15 s per acquisition) for an additional 2 min. to characterize the wash-out slope of the kinetic curve. Total scan time for the entire protocol was less than 45 min.

Multiparametric Breast MRI Segmentation and Comparison

The nonlinear dimensionality reduction (NLDR) methods of the present invention were applied to the breast MRI data and an embedded image and scattergram were generated per such methods. To differentiate tissue types and soft boundaries between them, a continuous red-green-blue (RGB) color code was assigned to the embedded image. Also, to perform a quantitative comparison between the embedded image and ground truth, similarity measures were used based on regional overlap between hard boundaries. Ground truth was based on the current clinical standard in breast imaging, which is the post contrast MRI.

A Dice similarity index was used, which was designed to find the overlapping regions between two objects (see FIG. 4B). In this application, A and B are lesion areas obtained by ground truth (postcontrast image) and the embedded image, respectively. The lesion area for the postcontrast was obtained by thresholding of the contrast image.

The threshold was obtained by evaluating the postcontrast MR image histogram, and using a mean and a 95% confidence interval. The embedded image, however, returned a fuzzy boundary with the RGB color code. The hard boundary was obtained by converting the embedded image to a binary image and assigning a "1" to the red color-coded pixels and a zero to the pixels with other colors. If A and B have full overlap, then the DS=1.0. But if A and B do not intersect, then the DS=0. To evaluate the DR methods, they were applied to segment and visualize breast tumors using multiparametric MRI data in a small series of patients and volunteers to discern the properties of each MR sequence in breast lesion identification. It should be noted that no classification was performed.

RESULTS

Synthetic Data

Figure 6:
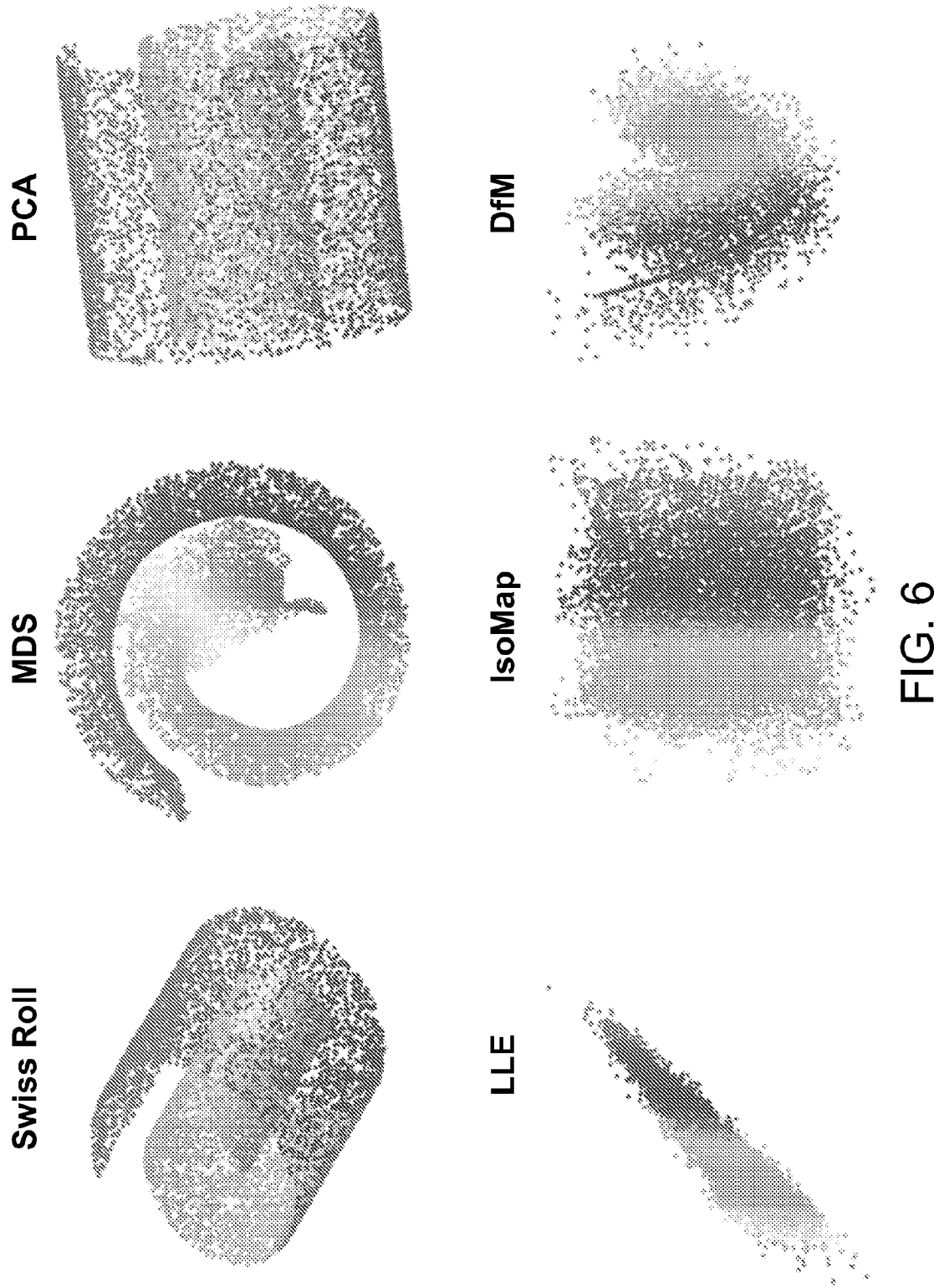
FIG. 6 provides illustrative views showing a dimension reduction of the Swiss Roll from 3 to 2 dimensions using MDS, PCA, LLE) Isomap and diffusion maps (DfM). Neighborhood size for LLE and Isomap, respectively, were 5 and 10. Sigma for DfM was 0.2. The linear methods (MDS and PCA) both failed to unfold the Swiss Roll in the reduced dimension, while all nonlinear methods (LLE, Isomap, and DfM) were able to unfold the data and preserve structure. The best result was obtained by Isomap.

There is shown in FIG. 6 typical results for the DR methods applied to the Swiss Roll manifold. Both linear methods (i.e., PCA and MDS) failed to unfold the manifold and preserve structure when mapping from 3 to 2 dimensions. The nonlinear method, Isomap, was able to unfold the Swiss roll with good results. Both the LEE and DfM methods were able, in part, to unfold the Swiss roll with most of the structure retained.

Figure 7:
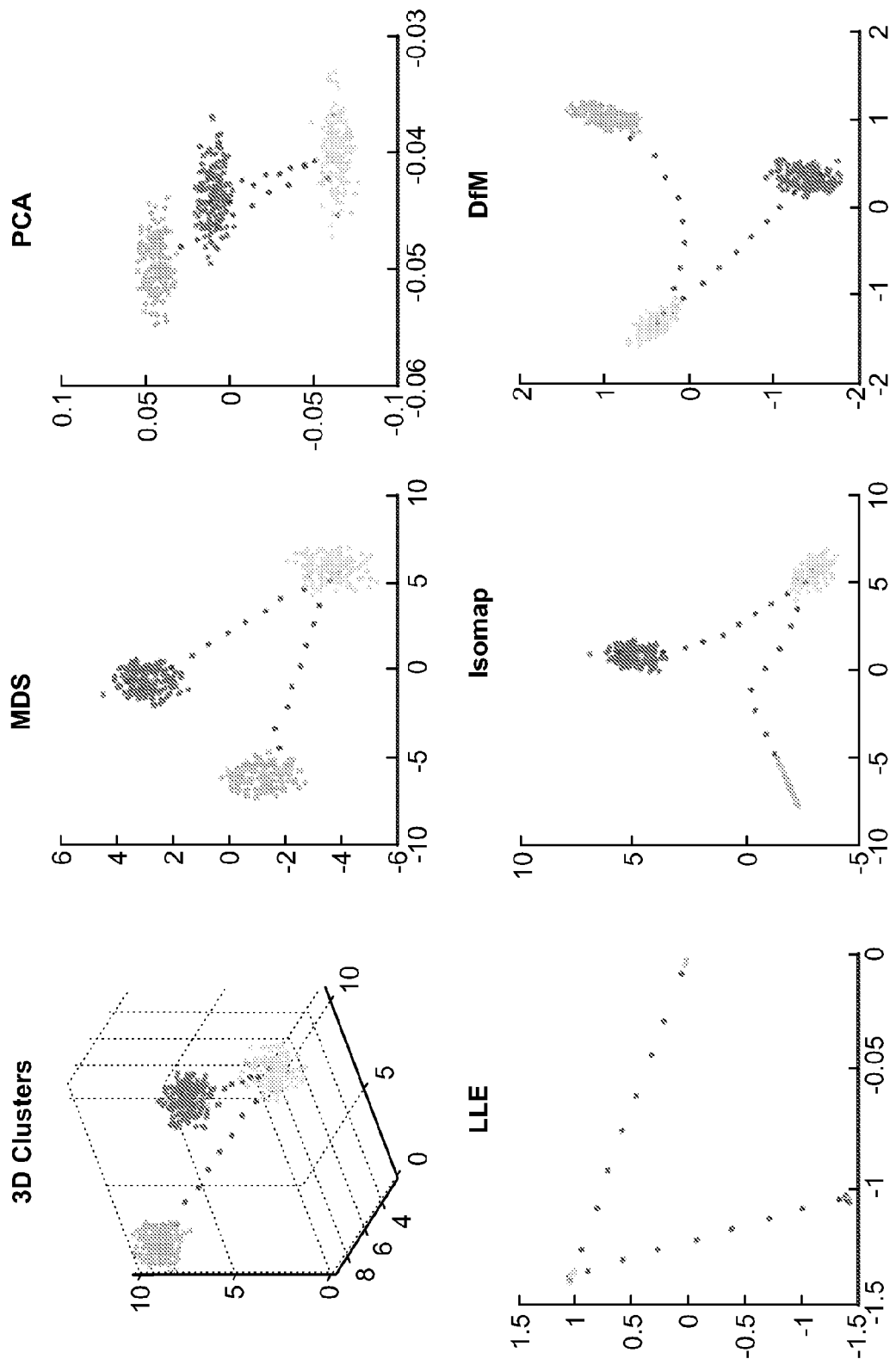
FIG. 7 provides various graphical views providing demonstration of dimension reduction of 3D clusters (a) from 3 to 2 dimensions using MDS, PCA, LLE, Isomap and diffusion maps (DfM). Sigma for DfM was 0.2. Neighborhood size for LLE and Isomap, respectively, were 5 and 10. In this example, all methods except LLE were able to preserve clusters in the reduced dimension. Isomap was not able to fully preserve structure of for the cyan color cluster in the embedding space. LLE was not able to preserve structure of all three clusters and converted the clusters to points in the embedding space.
Figure 8:
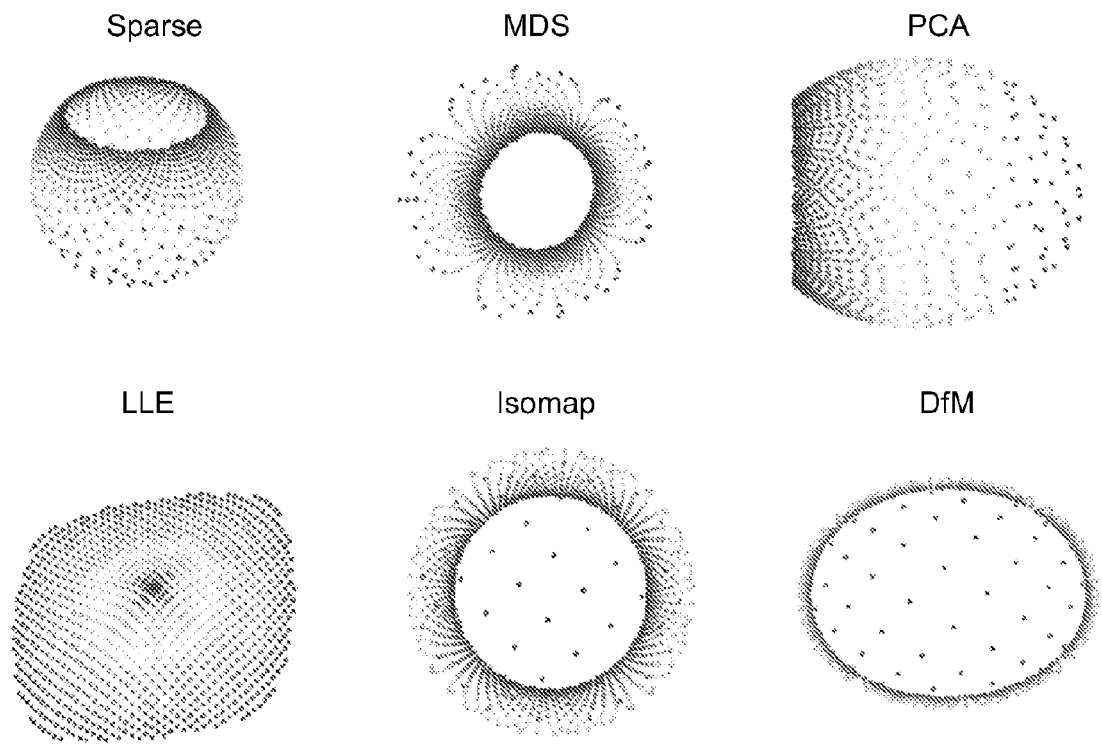
FIG. 8 illustrates embedding of sparse data (a) from 3 to 2 dimensions using MDS, PCA, LLE, Isomap and diffusion maps (DfM). Neighborhood size for LLE and Isomap, respectively, were 5 and 10. Sigma for DfM was 0.2. Both linear methods (MDS and PCA) failed to preserve the sparse data structure in the reduced dimension. DfM was able to fully preserve the sparse data pattern in the embedding space. LLE successfully mapped the sparse data structure to the embedded space. Isomap also was able to preserve most of the data structure but was unable to correctly map all the blue color to the embedding space.
Figure 9:
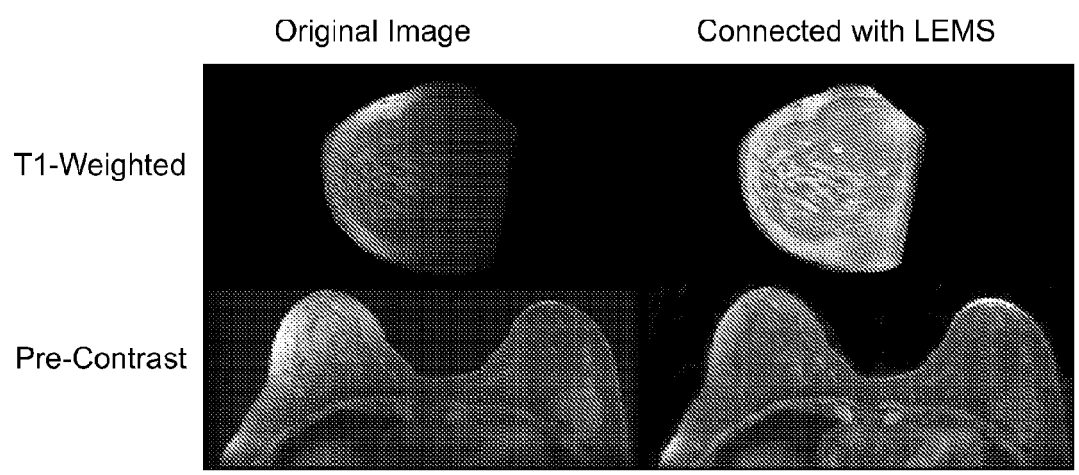
FIG. 9 is a pictorial view showing correction of $B_1$ inhomogeneity in the MRI data with the local entropy minimization with a bicubic spline model (LEMS) method: Shown are original and corrected images, respectively, for T1-weighted images. After correction, better visualization of breast tissues is noted and they isointense across the image, compared with the images on the left.

In the 3D point cluster model, most of the linear and nonlinear DR methods, with the exception of LLE, were able to maintain the 3D cluster structure when mapped to the lower dimension, as demonstrated in FIG. 7. Notably, LLE converted each cluster to points. Finally, the sparse (non-uniform) manifold data revealed the main difference and the power of nonlinear DR methods compared to linear methods, as shown in FIG. 8. The linear methods failed to unfold the sparse data set, whereas, the nonlinear DR methods were able to preserve, in most cases, the structure of the sparse manifold. In particular, LLE performed the best, but Isomap and DfM were able to partially preserve the structure.

Multiparametric Breast MRI Preprocessing Steps

Figure 4A:
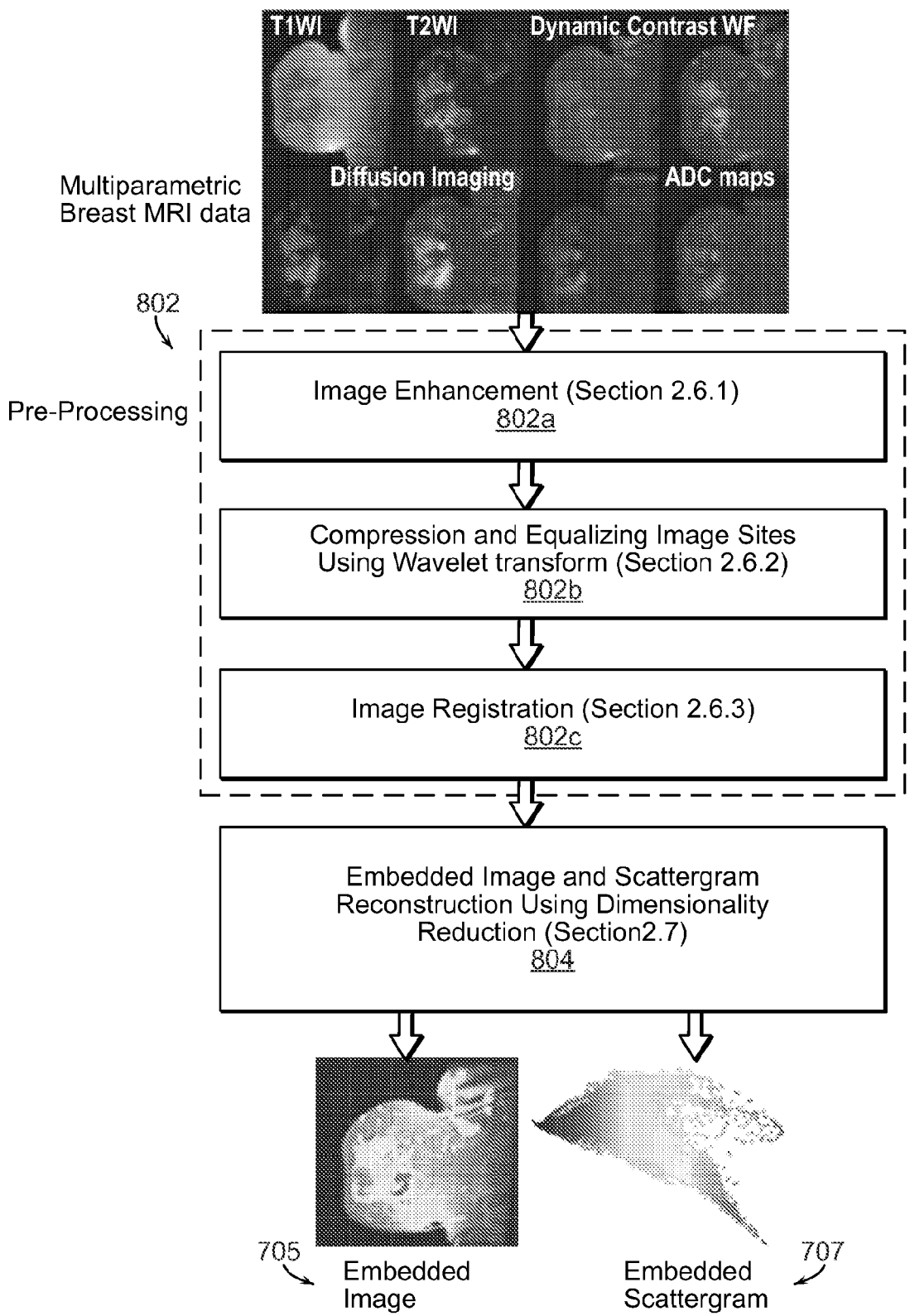
FIGS. 4A, B—provide a proposed schema or methodology for multidimensional image data integration using the NLDR methods to construct the embedded image and soft tissue segmentation (FIG. 4A) and a proposed schema for extraction of tumor hard boundaries for direct comparison with the postcontrast image as the current standard technique (FIG. 4B). The same procedure is used for the other breast tissue (fatty and glandular).
Figure 4B:
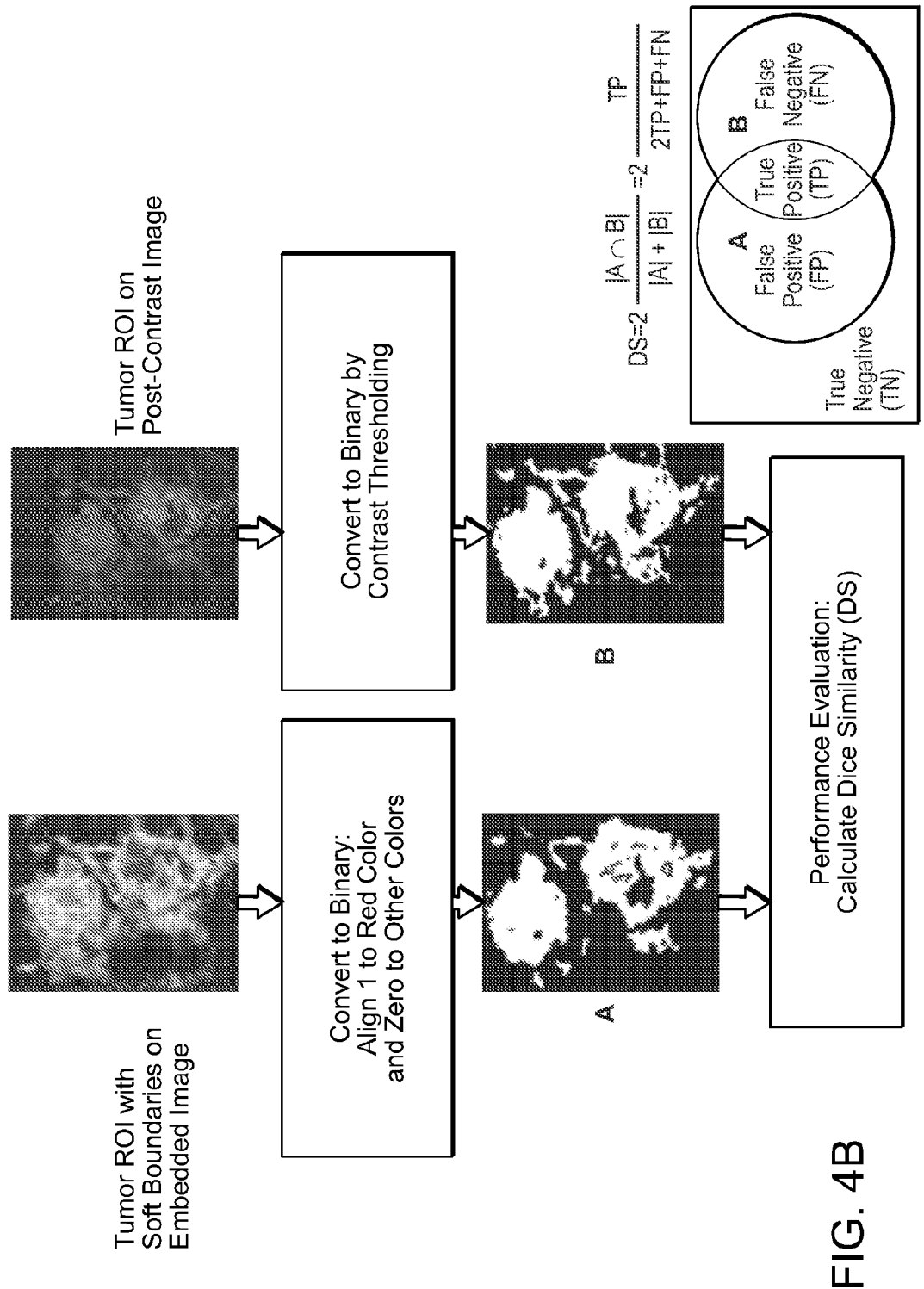
Figure 5A:
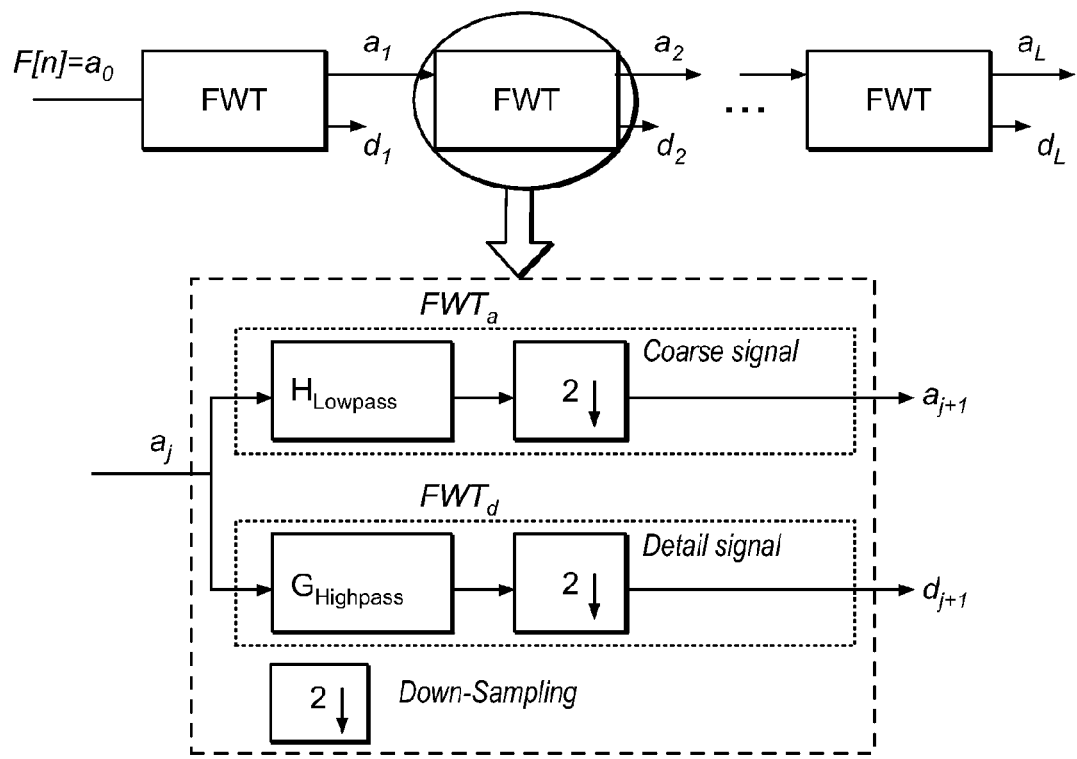
FIGS. 5A-D are various views of signal (FIG. 5A) and image (FIG. 5B) decomposition using FWT and signal (FIG. 5C) and image (FIG. 5D) reconstruction using IFWT, $a_0$ is original signal (image). $a_j$ and $d_j$, respectively, are the approximation (coarse or low pass) and detail (high pass) components corresponding to vertical, horizontal, and diagonal at decomposition level j.
Figure 5B:
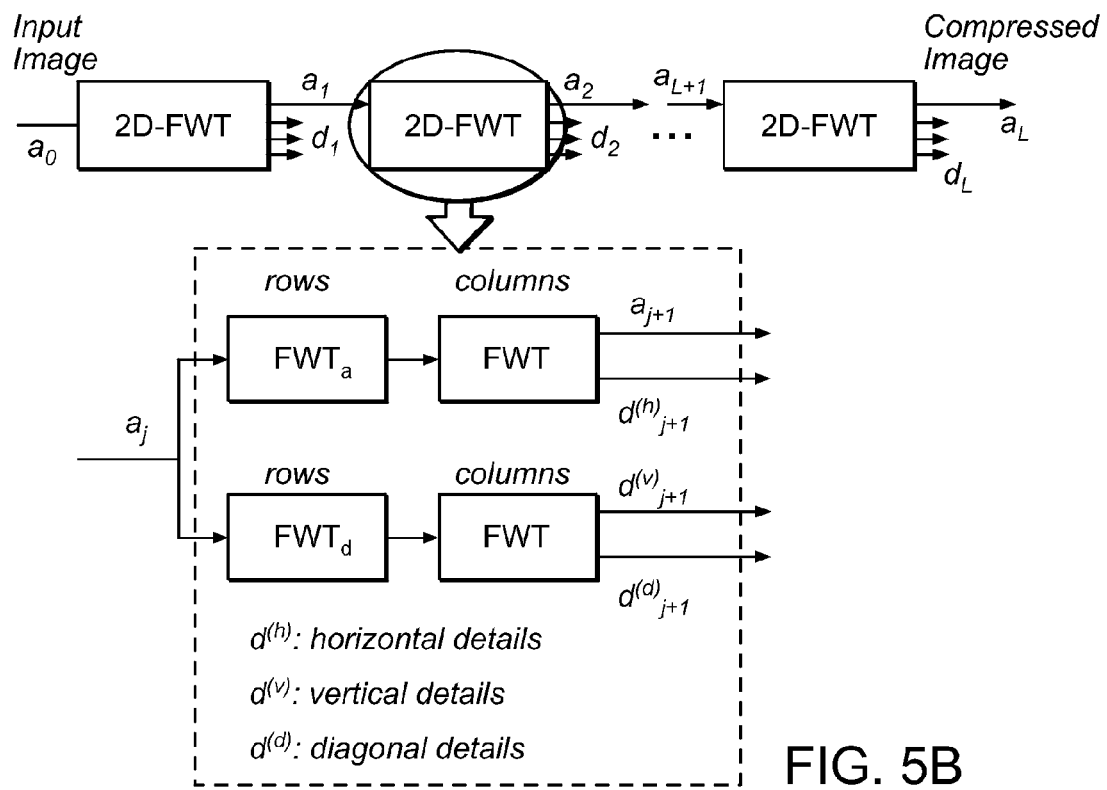
Figure 5C:
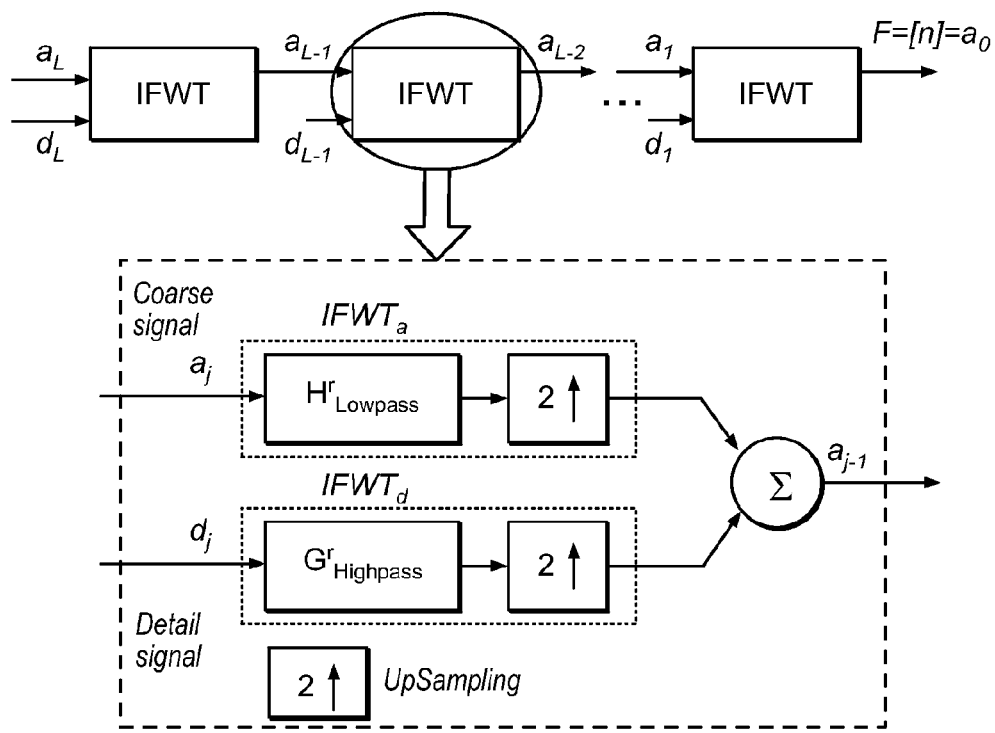
Figure 5D:
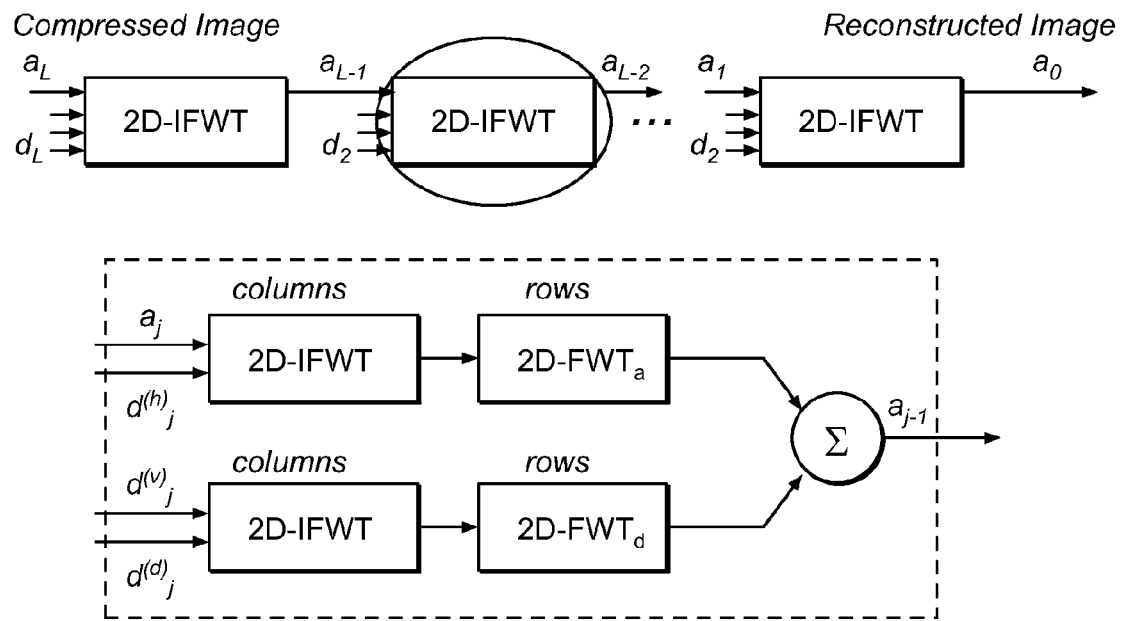
Figure 10:
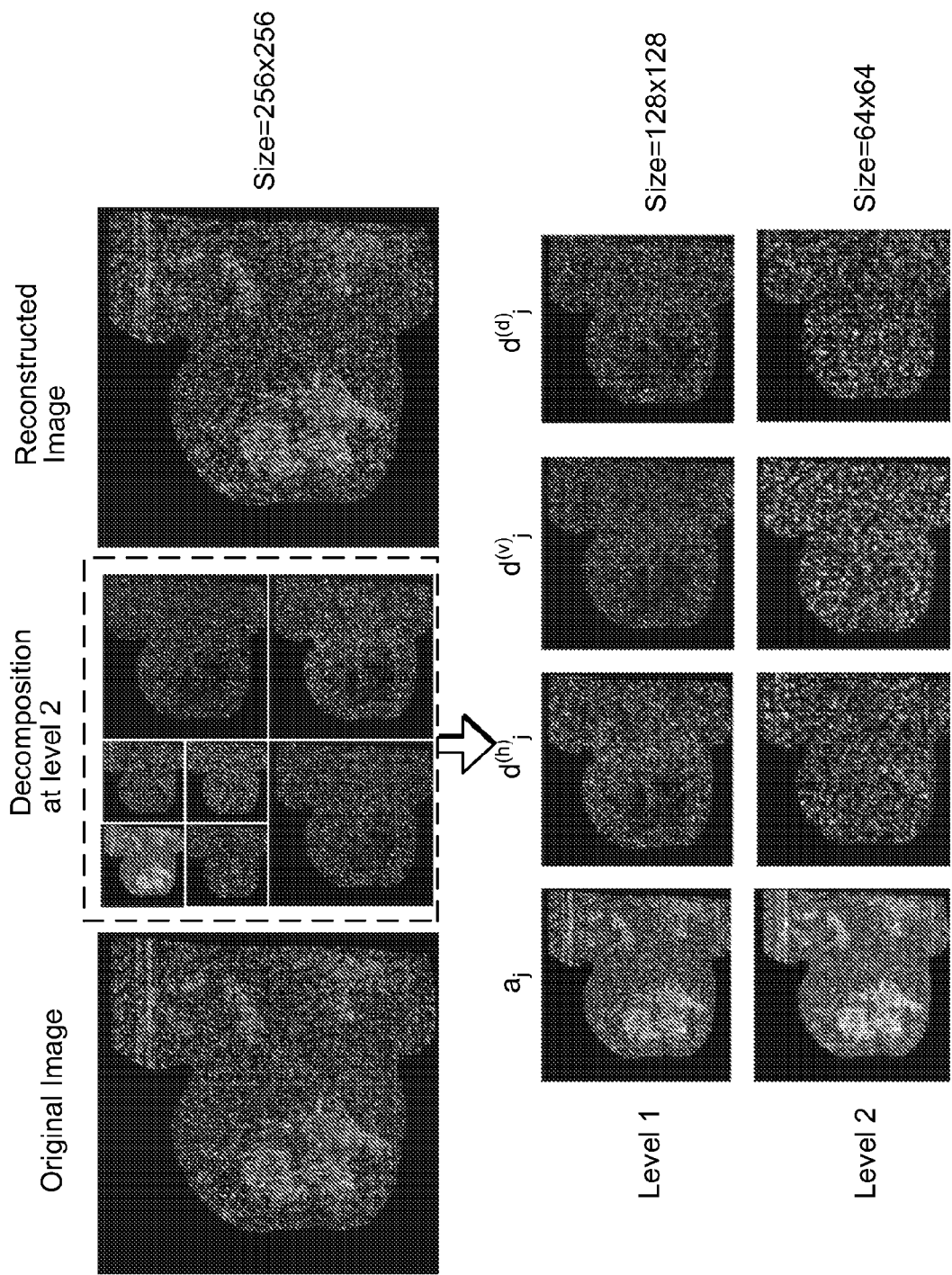
FIG. 10 provides various pictorial views of typical diffusion-weighted image (b=500) in the original size 256×256, after compression (64×64) and decompression (reconstructed image: 256×256). For compression, 2D bi-orthogonal spline wavelets were used. $d_j^{(k)}$, $d_j^{(v)}$ and $d_j^{(d)}$, respectively, are detail components corresponding to vertical, horizontal, and diagonal $a_j$, is the approximation (coarse) component at decomposition level j.
Figures 11D, 11E:
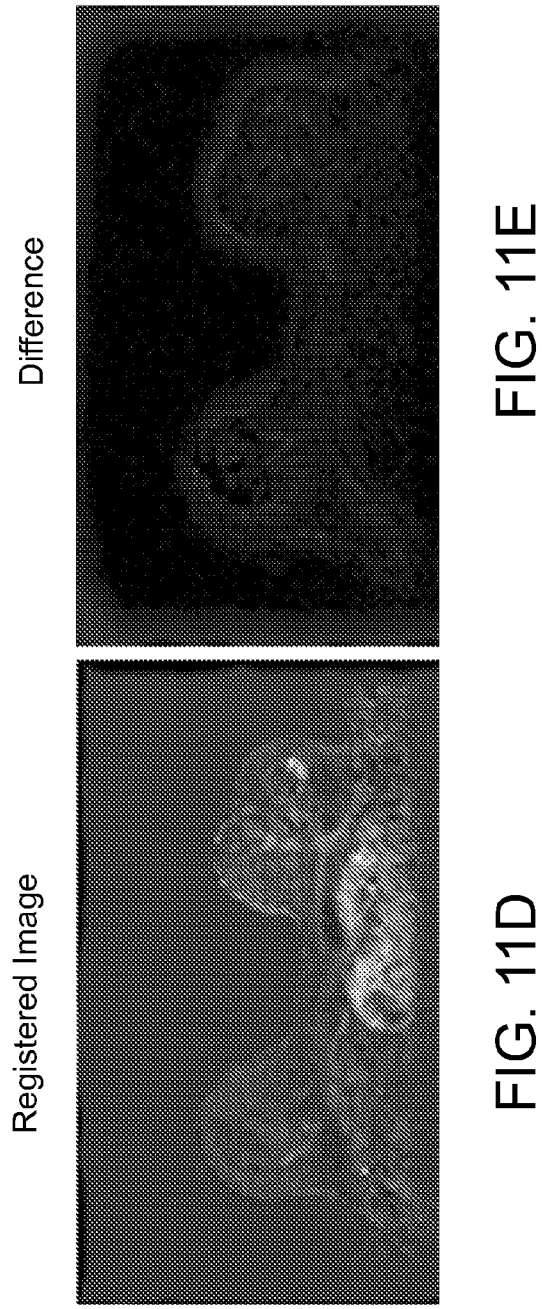

Based on the results from the synthetic data, the nonlinear methods were applied to the multiparametric breast data using the DR integration scheme outlined in FIG. 4A. The preprocessing of the T1WI (sagittal and axial) before and after B1 inhomogeneity correction is shown in FIG. 19. The coefficients of variation (COV) for fatty tissue, as an example, before applying LEMS, were 98.6 and 67.2, respectively, for T1WI and precontrast MRI images. The COV improved to 49.3 and 39.2, after correction. The wavelet compression and decompression methods applied to a DWI (b=500) image are demonstrated in FIG. 10. The original size was 256×256, and was resized (compressed and decompressed) to 64×64. The reconstructed image was identical to the original image with no errors.

The registration of the breast MRI was achieved using a locally affine model, and typical results are shown in FIG. 11A-E. The mean square error between the predicted intensity map of the reference image and original reference image was 0.0567.

Multiparametric Breast MRI Segmentation

The power of using nonlinear embedding of multiparametric breast MRI in several dimensions is demonstrated in FIGS. 12 A, B and 13 A, B. For example, in FIG. 12, there are nine dimensions: T1WI; T2WI; precontrast; postcontrast; DWI (4-b values) and ADC maps into a single image that provided a quantitative map of the different tissue types for abnormal (malignant) and normal tissue. All images were resized to 256×256 using the methods outlined in FIGS. 5A-D. After scaling the intensity of the embedded images (range of 0-1000), the lesion tissue appeared red, with normal fatty tissue appearing blue. The embedded scattergram was useful in classifying the different tissue types (see FIGS. 12 and 13).

The Dice similarity index between the lesion contours defined by the embedded image demonstrated excellent overlap (>80%) with the DCE-MRI-defined lesion.

Comparison of the computational loads for the NLDR methods indicated that the load for Isomap was very high compared to DfM and LLE. For example, for breast MRI images with a matrix size of 256×256, the computation times for DfM, Isomap, and LLE were 19.2, 508.4, and 78.6 seconds, respectively, using an Intel quad-core microprocessor with 8 Gb RAM and an Nvidia Quadro 4000 (256 cores, 2 GB) video card.

Figure 14C:
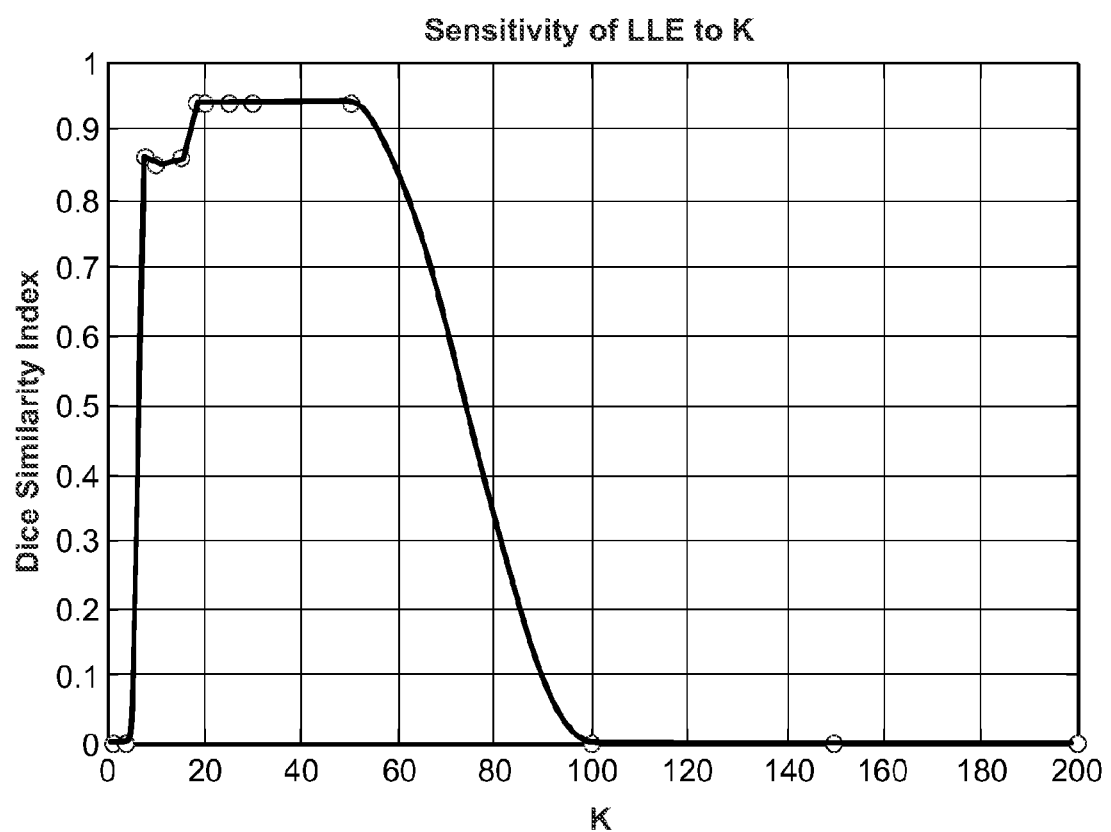

To determine the robustness of the NLDR methods to their input parameters, the different input parameters were varied. These parameters are defined in Isomap and LLE as the neighborhood size [K], and defined in DfM as the sigma parameter. There is shown in FIGS. 14A-C, how the Dice similarity index changed with each of the NLDR parameter [neighborhood size [K] in Isomap and LLE; sigma in DfM] variations. As shown, the neighborhood size K for Isomap should be chosen to be greater than 10, and, for LLE, it should vary from 20 to 60. However, the DfM is very sensitive to sigma in the Gaussian kernel, and, based on our investigations, sigma should range between 100 and 1000, but a sigma of at least 100 would be sufficient for complex data, such as MRI.

DISCUSSION

A hybrid scheme was developed using NLDR methods to integrate multiple breast MRI data into a single embedded image. The resultant embedded image enabled the visualization and segmentation of breast lesions from the adjacent normal breast tissue with excellent overlap and similarity.

The performance of both linear and nonlinear DR methods were compared using synthetic and multiparametric breast MRI, to determine which DR method to use. When using synthetic data, the three nonlinear DR methods, namely DfM, Isomap, and LLE, outperformed the linear methods (PCA and MDS) in all categories. The NLDR methods, in general, were able to segment and visualize the underlying structure of the Swiss Roll, point clouds, and, more importantly, sparse data. This is important because the sparse data represents a real-world scenario and the NLDR methods were able to unfold the underlying structure. Thus, the NLDR methods were chosen for the breast data.

Multiparametric breast data represent complex high-dimensional data, and no single parameter conveys all the necessary information. Integration of the breast parameters is required and the methods of the present invention provide an opportunity to achieve such integration. The reported results demonstrate that when the NLDR methods are applied to breast MRI data, the DR methods were able segment the lesion and provide excellent visualization of the tissue structure.

This mapping of high-dimensional data to a lower dimension provides a mechanism to explore the underlying contribution of each MR parameter to the final output image. Indeed, each one of these methods is designed to preserve different data structures when mapping from higher dimensions to lower dimensions. In particular, DfM and Isomap primarily emphasize the global structure within the multidimensional feature space and are less sensitive to variations in local structure. However, LLE has greater sensitivity to the variations in local structure and is less sensitive to variations in global structure. In general, DfM and Isomap returned images similar to the embedded images from LEE, using the breast MRI data. Therefore, each of the methods was able to differentiate the breast lesion cluster within the scattergram, suggesting that, for computer-assisted diagnosis, either of the three DR methods (DfM and Isomap for global structures and LLE for local structures) could be applied to better assist the radiologist in decision-making.

This was confirmed by the congruence between each embedded image and breast DCE MRI with the Dice similarity metric. The Dice similarity metric showed excellent results with a little variation in the segmented lesion areas between the embedded and DCE MRI. One potential advantage of using an embedded image created from the breast MRI would be to create tissue masks for automatic overlay onto functional MRI parameters, such as ADC or sodium maps to develop an automatic quantification system that could be used to monitor treatment response [M. A. Jacobs, A. C. Wolff, R. Ouwerkerk, S. Jeter, E. Gaberialson, H. Warzecha, D. A. Bluemke, R. L. Wahl, and V. Stearns, "Monitoring of neoadjuvant chemotherapy using multiparametric, (23) Na sodium MR, and multimodality (PET/CT/MRI) imaging in locally advanced breast cancer," Breast Cancer Res. Treat. 128(1), 119-126 (2011)].

Other applications for DR methods with MRI data that have been published include the differentiation of benign and malignant tissue on magnetic resonance spectroscopy (MRS) data. Tiwari et al. [P. Tiwari, M. Rosen, and A. Madabhushi, "A hierarchical spectral clustering and nonlinear dimensionality reduction scheme for detection of prostate cancer from magnetic resonance spectroscopy (MRS)," 36(9), 3927-3939 (2009)] used DR methods to separate the different peaks of metabolites (choline, citrate, etc.) into different classes and then overlaid the results onto the T2WI of the prostate with increased sensitivity and specificity. However, these investigators only utilized the frequency domain of the spectra and not the entire dimensionality of the prostate data set, that is, combined MRI and MRS.

Six types of DR techniques (three linear and three nonlinear techniques) were compared using both real and synthetic data and use the power of the DR methods to segment breast tissue and create an embedding image of each parameter. In another report, Richards et al. [W. Richards, P. E. Freeman, A. B. Lee, and C. M. Schafer, "Exploiting low-dimensional structure in astronomical spectra," Astrophys. J. 691(1), 32-42 (2009)], demonstrated that DfM outperformed PCA (linear DR) in the classification of galaxy red-shift spectra when used as input in a regression risk model.

In addition, DfM gave better visualization of the reparameterized red-shift separation in the embedded image, but both methods were able to separate the first few components to identify the different subgroups, which are consistent with our results. A method to reconstruct an embedded image from the higher-dimension MRI data space into a reduced (embedded) dimension to use for tumor segmentation and visualization has been demonstrated. Moreover, to deal with the high computational load of DR, the stability of each method in relation to the input parameters was tested to determine the optimal range for correct segmentation as defined by the current clinical imaging standard and found ranges that can be utilized for as starting points for other applications using breast MRI or other related data sets.

In summary, by combining different MRI sequences, using dimensionality reduction and manifold learning techniques, there has been developed a robust and fully automated tumor segmentation and visualization method. This approach can be extended to facilitate large-scale multiparametric/multimodal medical imaging studies designed to visualize and quantify different pathologies [M. A. Jacobs, "Multiparametric magnetic resonance imaging of breast cancer," J. Am. Coll. Radiol. 6(7), 523-526 (2009)].

As indicated herein, such methods of the present invention are suitable for use in combination with any of a number of computer systems as are known to those skilled in the art or hereinafter developed such as that described herein. Such a computer system includes a computer, a display, and one or more input device(s). The display is any of a number of devices known to those skilled in the art for displaying images responsive to outputs signals from the computer, including but not limited to cathode ray tubes (CRT), liquid crystal displays (LCDS), plasma screens and the like. It should be recognized that the signals being outputted from the computer can originate from any of a number of devices including PCI or AGP video boards or cards mounted with the housing of the computer that are operably coupled to the computer's microprocessor and the display. As indicated herein, such video boards or cards should be configured so as to have sufficient capacity (e.g., cache memory and processing speed) to process and display the images in near real time. As indicated herein, the apparatus on which the software program or applications program can be executed includes in addition to the computer, a microprocessor, a digital processor, an ASIC or the like.

The one or more input device(s) are any of a number of devices known to those skilled in the art which can be used to provide input signals to the computer for control of applications programs and other programs such as the operating system being executed within the computer. In illustrative embodiments, the input device preferably comprises a switch, a slide, a mouse, a track ball, a glide point or a joystick or other such device (e.g., a keyboard having an integrally mounted glide point or mouse) by which a user such as student can input control signals other than by means of a keyboard.

The computer typically includes a central processing unit including one or more micro-processors such as those manufactured by Intel or AMD, Motorola or the like, random access memory (RAM), mechanisms and structures for performing I/O operations, a storage medium such as a magnetic hard disk drive(s) or other drives (fixed or removable) for storage of data, operating systems or the applications or software programs of the present invention including a software program or an applications program according to the present invention(s), and a device (not shown) for reading from and/or writing to a removable computer readable medium, such as for example an optical disk reader capable of reading CDROM, DVD or optical disks and readers of other types of nonvolatile memory such as flash drives, jump drives or spin memory that embody one or more types of non-volatile types of memory or storage devices. As indicated herein, in particular embodiments the microprocessor is preferably a multi-core type of processor having sufficient processing capability and speed as well as RAM so as to perform the method steps described herein.

Such a hard disk drive is provided for purposes of booting and storing the operating system, other applications or systems that are to be executed on the computer, paging and swapping between the hard disk and the RAM and the like. In this embodiment, an applications program according to the present invention is stored in the hard drive including the programming instructions and a data portion containing the text, auditory and visual informational data being displayed as well as the historical file of such information. Such data also can be stored in a removable computer readable medium such as a CD or DVD type of media that is inserted into a device for reading and/or writing to the removable computer readable media. Such a reading/writing device is any of a number of devices known to those skilled in the art for reading from and/or writing to the particular medium on which the applications program is stored.

In an alternative embodiment, such a computer system also includes a network based computer system that includes a server, an external storage device and a network infrastructure that operably couples a plurality or more of client computer systems to the server. The client computer systems are typically configured like the above described computer system except that in use the applications program of the present invention and related data of a condition for a given individual could be found on the server and such information would be temporarily onto the client computer system.

The server is any of a number of servers known to those skilled in the art that are intended to be operably connected to a network so as to operably link a plurality or more of client computers via the network to the server and thus also to the external storage device. Such a server typically includes a central processing unit including one or more microprocessors such as those manufactured by Intel or AMD, random access memory (RAM), mechanisms and structures for performing I/O operations, a storage medium such as a magnetic hard disk drive(s), and an operating system for execution on the central processing unit. The hard disk drive of the server typically is not used for storing data and the like utilized by client applications being executed on the client computers. Rather the hard disk drive(s) of the server are typically provided for purposes of booting and storing the operating system, other applications or systems that are to be executed on the server, paging and swapping between the hard disk and the RAM.

Data and the like being used in connection with the execution of client applications, such as the applications program of the present invention and the information and/or data related thereto, can be stored in the external storage device that is operably interconnected to the server using any of a number of techniques and related devices or cabling known to those skilled in the art. In an illustrative embodiment, such an interconnection is implemented using a small computer systems interface (SCSI) technique(s) or via a fiber optic cable or other high-speed type of interconnection.

In an illustrative, exemplary embodiment, the external storage device comprises a disk assembly typically made up of one or more hard disks that are configured and arranged so the external storage medium functionally appears to the server as a single hard disk. Such an external storage medium is further configured and arranged to implement any of a number of storage schemes such as mirroring data on a duplicate disk (RAID level 1) or providing a mechanism by which data on one disk, which disk has become lost or inaccessible, can be reconstructed from the other disks comprising the storage medium (RAID level 5). Although reference is made to a disk assembly and hard disks, this is for illustration and shall not be construed as being a limitation on the particular form of the devices or mechanism that makes up the external storage device or the medium comprising such a device.

In addition, each of the client computers includes one or more I/O ports that are operably connected to the microprocessor and which are configured and arranged for the transfer of the data and program instructions between and amongst the client computer and the server using any of a number of non-wireless techniques or wireless techniques known to those skilled in the art. Such non-wireless techniques include for example any of a number of network infrastructures known to those skilled in the art such as Ethernet, token ring, FDDI, ATM, Sonet, X.25 and Broadband.

In the case of wireless techniques, the I/O ports of the client computers are configured so as to include a transceiver as is known to those skilled in the art for wireless network transmission systems. An exemplary wireless network technique includes those systems embodying a transceiver or transmitter complying with IEEE-802.11 or other appropriate standards hereinafter developed. In each case, the transceiver operably coupled to the client computer is configured and arranged so as to establish a communications link between the client computer and a receiver or transceiver remote from the location of the client computer that is in turn operably coupled to the server. The server in turn could be coupled to the remotely located transceiver/receiver using non-wireless or wireless techniques.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for segmentation and classification of radiological images, said method comprising the steps of:
   pre-processing of acquired image data;
   resizing a number of slices in a plurality of planes to a desired size using orthogonal reslicing; and
   reconstructing the acquired image data using a non-linear dimension reduction technique so as to yield an embedded image representing all of the acquired, where the acquired image data comprises a plurality of different sets of image data of the same region of interest.

2. The method of claim 1, wherein said preprocessing of image data includes compressing and equalizing image sizes using a wavelet transform.

3. The method of claim 2, wherein compressing and equalizing the image sizes includes using the hybrid affine.

4. The method of claim 1, wherein said preprocessing of image data includes registering each of the plurality of different sets of image data of the same region of interest.

5. The method of claim 4, wherein said registering includes processing each of the plurality of different sets of image data, wherein said processing includes
   registrating parameters estimation based on searching for best match between reference slices and target slices at a reslicing angle and plane, and
   non-uniform resampling including slice-by-slice angular reslicing and affine transformation of the target volume to another desired size using estimated registrating parameters.

6. The method of claim 1, wherein orthogonal reslicing is preformed via a hybrid affine and a wavelet method.

7. A system for segmentation and classification of radiological images, comprising:
   a microprocessor; and
   software program for execution on the microprocessor, said software program comprising code elements, criteria and instructions in a form that instructs the microprocessor to perform functions of:
   pre-processing of acquired image data;
   resizing a number of slices in a plurality of planes to a desired size using orthogonal reslicing; and
   reconstructing the acquired image data using a non-linear dimension reduction technique so as to yield an embedded image representing all of the acquired, where the acquired image data comprises a plurality of different sets of image data of the same region of interest.

8. The system of claim 7, wherein said preprocessing of image data includes compressing and equalizing image sizes using a wavelet transform.

9. The system of claim 7, wherein said preprocessing of image data includes registering each of the plurality of different sets of image data of the same region of interest.

10. The system of claim 9, wherein said registering includes processing each of the plurality of different sets of image data, wherein said processing includes
    registrating parameters estimation based on searching for best match between reference slices and target slices at a reslicing angle and plane, and
    non-uniform resampling including slice-by-slice angular reslicing and affine transformation of the target volume to another desired size using estimated registrating parameters.

11. A method for segmentation and classification of radiological images, said method comprising the steps of:
    pre-processing of acquired image data including registering and thereby processing each of the plurality of different sets of image data of the same region of interest further comprising:
    resizing number of slices in all planes to a desired size using orthogonal reslicing,
    registrating parameters estimation based on searching for best match between reference slices and target slices at a reslicing angle and plane, and
    non-uniform resampling including slice-by-slice angular reslicing and affine transformation of the target volume to another desired size using estimated registrating parameters; and
    reconstructing the acquired image data using a non-linear dimension reduction technique so as to yield an embedded image representing all of the acquired, where the acquired image data comprises a plurality of different sets of image data of the same region of interest.

12. A system for segmentation and classification of radiological images, comprising:
    a microprocessor; and
    software program for execution on the microprocessor, said software program comprising code elements, criteria and instructions in a form that instructs the microprocessor to perform functions of:
    pre-processing of acquired image data including registering each of the plurality of different sets of image data of the same region of interest further comprising:
    resizing number of slices in all planes to a desired size using orthogonal reslicing,
    registrating parameters estimation based on searching for best match between reference slices and target slices at a reslicing angle and plane, and
    non-uniform resampling including slice-by-slice angular reslicing and affine transformation of the target volume to another desired size using estimated registrating parameters; and
    reconstructing the acquired image data using a non-linear dimension reduction technique so as to yield an embedded image representing all of the acquired, where the acquired image data comprises a plurality of different sets of image data of the same region of interest.

* * * * *